United States Patent
Blau et al.

(10) Patent No.: US 7,754,202 B1
(45) Date of Patent: Jul. 13, 2010

(54) METHODS OF CONTROLLING CELL DIFFERENTIATION AND GROWTH USING A FUSION PROTEIN AND A DRUG

(75) Inventors: Carl Anthony Blau, Seattle, WA (US); David M. Spencer, Houston, TX (US)

(73) Assignees: Stanford University, Palo Alto, CA (US); University of Washington, Seattle, WA (US)

( * ) Notice: Subject to any disclaimer, the term of this patent is extended or adjusted under 35 U.S.C. 154(b) by 0 days.

(21) Appl. No.: 09/582,916

(22) PCT Filed: Jan. 7, 1999

(86) PCT No.: PCT/US99/00348

§ 371 (c)(1),
(2), (4) Date: Oct. 2, 2000

(87) PCT Pub. No.: WO99/34836

PCT Pub. Date: Jul. 15, 1999

Related U.S. Application Data

(60) Provisional application No. 60/070,754, filed on Jan. 8, 1998, provisional application No. 60/070,893, filed on Jan. 9, 1998, provisional application No. 60/102,888, filed on Oct. 2, 1998.

(51) Int. Cl.
*A61K 48/00* (2006.01)
*C12N 5/00* (2006.01)
*C12N 15/63* (2006.01)

(52) U.S. Cl. .................. 424/93.21; 514/44 R; 435/325; 435/320.1; 435/455

(58) Field of Classification Search ............. 435/320.1, 435/325, 326, 455; 424/93.1, 93.21; 514/44 R
See application file for complete search history.

(56) References Cited

U.S. PATENT DOCUMENTS 5,741,899 A * 4/1998 Capon ........................ 36/23.4
5,994,313 A * 11/1999 Crabtree et al. ............... 514/31
6,150,527 A * 11/2000 Holt et al. .................... 546/189
6,506,379 B1  1/2003 Clackson

OTHER PUBLICATIONS

Musk et al. (1995) J. Cell. Biochem., Suppl. 21A.*
Blau et al. (1997) PNAS, vol. 94, 3076-3081.*
Spencer et al. (1996) Current Biology, vol. 6(7), 839-847.*
Blau et al. (1996) Blood, vol. 88 (10 Suppl. 1 part 1-2), p. 542A.*
Ramsfjell et al. (1996) Blood, vol. 88 (12), 4481-4492.*
Blau, C.A. et al., "A proliferation switch for genetically modified cells," *Proc. Natl. Acad. Sci. USA* 94:3076-3081, 1997.
Palacios, R. and M. Steinmetz, "IL3-Dependent Mouse Clones That Express B-220 Surface Antigen, Contain Ig Genes in Germ-Line Configuration, and Generate B Lymphocytes in Vivo," *Cell* 41:727-734, 1985.
Simmons, N.L., "A Cultured Human Renal Epithelioid Cell Line Responsive to Vasoactive Intestinal Peptide," *Experimental Physiology* 75: 309-319, 1990.
Yang, J. et al., "Small-molecule control of insulin and PDGF receptor signaling and the role of membrane attachment," *Current Biology* 8(1):11-18, 1997.
Kudla, Arthur J., et al., "The FGF Receptor-1 Tyrosine Kinase Domain Regulates Myogenesis but Is Not Sufficient to Stimulate Proliferation," *The Journal of Cell Biology*, 142(1):241-250, 1998.
Spencer, David M., "Controlling Signal Transduction With Synthetic Ligands," *Science* 262:1019-1024, Nov. 12, 1993.
Goncalves, F., et al., "Thrombopoietin Does Not Induce Lineage-Restricted Commitment of Mpl-R Expressing Pluripotent Progenitors but Permits Their Complete Erythroid and Megakaryocytic Differentiation," *Blood* 80(10):3544-3553, 1997.
Rivera, V.M., et al., "A Humanized System for Pharmacologic Control of Gene Expression," *Nature Medicine* 2(9):1028-1032, 1996.

* cited by examiner

*Primary Examiner*—Anne Marie S Wehbe
(74) *Attorney, Agent, or Firm*—Nixon Peabody LLP

(57) ABSTRACT

This invention involves methods and materials for conferring a direct proliferative advantage on a genetically modified subpopulation of cells. Selection is then accomplished by exerting a positive selective stimulus on the engineered cells rather than a negative pressure on nonengineered cells.

32 Claims, 6 Drawing Sheets

- ■ Myristylation peptide
- ▩ FKBP12
- ▨ C-*mpl* receptor
- ☐ HA epitope

METHODS OF CONTROLLING CELL DIFFERENTIATION AND GROWTH USING A FUSION PROTEIN AND A DRUG

CROSS-REFERENCES TO RELATED APPLICATIONS

This application claims the benefit of U.S. Provisional Application No. 60/070,754, filed Jan. 8, 1998; U.S. Provisional Application No. 60/070,893, filed Jan. 9, 1998; and U.S. Provisional Application No. 60/102,888, filed Oct. 2, 1998.

FIELD OF THE INVENTION

This invention is directed to methods and materials that may be used in vitro or in vivo to confer a direct proliferative advantage on a genetically modified subpopulation of primary mammalian cells in response to a drug.

BACKGROUND OF THE INVENTION

The inefficiency of gene transfer is one of the factors limiting the practice of gene therapy. In some applications, e.g., genetic engineering of early progenitor and stem cells, it has been a major obstacle. Enrichment of a minor population of genetically modified cells by selection of transduced cells provides one avenue, at least in vitro, for overcoming such inefficiencies. One approach for selection involves using a vector in which a gene encoding a selectable product is coupled with a gene encoding a therapeutic protein; selection of cells based on the presence of the selectable product permits the emergence of the subpopulation of cells containing the therapeutic gene (Migita, et al. *Proc. Natl. Acad. Sci. USA* 92:12075, 1995). Selection may be applied ex vivo (Migita, et al. *Proc. Natl. Acad. Sci. USA* 92:12075, 1995) or, if a clinically tolerable regimen were devised, repeated cycles of selection might be under-taken in vivo. (See Sorrentino, et al. *Science* 257:99, 1992). Conventional methods for selection involve the transfer of a gene encoding a product which confers resistance to a cytotoxic drug. Exposure of the cells to the corresponding cytotoxic drug permits selective growth of only those cells transduced with the drug resistance gene.

The clinical applicability of this approach is limited by at least two factors. First, cytotoxic drugs have undesired consequences for the recipient when administered in vivo. Second, the persistent enrichment of genetically modified cells is expected to require that selection be exerted at the level of uncommitted cells. However, selective pressure is very difficult to apply at the level of progenitors and stem cells due to their intrinsic resistance to killing by most cytotoxic agents (Blau, et al. *Hum. Gen. Ther.* 7:2069, 1996; Allay, et al. *Blood* 90:3546, 1997).

New methods and materials for selecting a desired subpopulation of cells would be useful in a variety of biological research contexts and could be of particularly great value in clinical applications, especially if the use of cytotoxic drug or other agents with unwanted pharmacologic activities can be avoided.

SUMMARY OF THE INVENTION

This invention represents a marked departure from previous attempts to genetically modify cells, including stem cells and other early progenitor cells. As described above, current practices in the art include the introduction into cells of a desired gene along with a selectable marker. Transduced cells are then selected based on their resistance to killing by a cytotoxic drug. However, cytotoxic drugs have unwanted effects on other cells and are often less effective against less differentiated cells, even in the absence of genetic engineering.

In contrast to such approaches, this invention is based on conferring a direct proliferative advantage on the genetically modified subpopulation of cells. Selection is then accomplished by exerting a positive selective stimulus on the engineered cells rather than a negative pressure on non-engineered cells (to which the engineered cells are less susceptible). The positive selective stimulus is provided, or at least initiated, by a small-molecule dimerizing drug, discussed at greater length below. Remarkably, this approach is effective not just in cultured cell lines, but also in primary mammalian cells, including for example, bone marrow cells, which contain stem cells and other progenitor cells.

Among other objectives, this invention thus provides a method for rendering a subpopulation of mammalian cells susceptible to drug-induced growth, proliferation and/or differentiation. This method, like the various other methods of the invention, involves transducing one or more cells of a population of mammalian cells, preferably primary mammalian cells, with at least one recombinant DNA construct encoding a specialized fusion protein to thus provide a transduced subpopulation of cells. The fusion proteins of this invention generally comprise at least one signaling domain and at least one drug-binding domain which is heterologous with respect to the signaling domain and binds to a selected drug. The fusion proteins are designed such that an appropriately chosen dimerizing agent (i.e., drug) binds to a molecule of the fusion protein and induces association of two or more molecules of fusion protein(s) to form a complex or assembly. Signaling domains of the fusion proteins are chosen based on their ability to initiate cellular signaling following multimerization. In practice, exposure of the transduced cells to the drug induces growth, proliferation and/or differentiation of the cells.

The cells which are to be engineered in accordance with this invention are mammalian cells, preferably human cells. Applications of the invention of particular significance involve the use of primary cells or tissue, including e.g., hemopoietic cells, embryonic stem cells (Thomson, et al. *Science* 282:1145, 1998), hepatic cells, muscle cells, nerve cells, mesenchymal cells, cartilage and/or bone cells, intestinal cells, pancreatic cells or kidney cells, or a subpopulation of cells obtained therefrom. The cells to be engineered may be obtained from an embryonic, juvenile or adult mammal and, in a number of embodiments of the invention, preferably comprise stem, precursor and/or progenitor cells. In illustrative applications of the invention, the cells are bone marrow cells, cord blood cells or peripheral blood cells which include hemopoietic stem cells, precursor cells and/or progenitor cells, or a subpopulation of cells obtained therefrom.

In one approach, the cells are first removed from a mammal and are then transduced with the recombinant DNA construct(s). A variety of systems have been developed which permit the genetic engineering of cells, both in vivo and ex vivo, to allow dimerizer-mediated regulation of biological events (although heretofore, none have been applied to the expansion of a subpopulation of cells as provided herein). See, e.g., WO 94/18317, WO 95/02684 and WO 96/41865. Materials and methods for implementing those systems are known in the art and may be adapted to the practice of the subject invention. Typically, the desired DNA constructs are incorporated into a DNA vector and introduced into the cells. Again, various methods and materials for doing so are known in the art and may be adapted to the practice of this invention, including the introduction of so-called "naked DNA" and the use of viral or other DNA vectors. Viral vectors useful in gene therapy are well-known and include, among others, retroviruses, vaccinia viruses, pox viruses, adenoviruses and adeno-associated viruses (AAV). Any viral or other DNA vector useful in gene therapy may be used in the practice of this invention. Typically, at least one DNA construct is introduced into the cells, encoding and capable of directing the expression of one or more fusion proteins capable of binding to the dimerizer and oligomerizing the signaling domains to achieve the desired biological response, for example, proliferation.

After the genetic engineering, the population of cells containing the transduced subpopulation of cells may be treated with dimerizer drug before and/or after their introduction into a recipient mammal. In one embodiment, prior to introduction of the cells into the recipient mammal, some or all of the non-transduced cells are allowed to die and/or are removed from the transduced subpopulation. The cells may be autologous, syngeneic or allogeneic with respect to the recipient. In the case of autologous cells, cells are obtained from a mammalian host, transduced (treated with dimerizing drug in certain embodiments) and returned to the same individual.

In another approach, the cells are transduced within the mammal, e.g., by administration of the recombinant DNA construct(s) to the mammal using any pharmaceutically acceptable means for the introduction of DNA. Preferably administration of the recombinant DNA construct(s) is effected using one or more viral vectors such as mentioned above. For in vivo gene therapy and other in vivo applications, the viral or other DNA vector containing the desired DNA construct(s) is administered to the mammal in a sufficient amount to transfect a sufficient number of cells and render them capable of drug-mediated growth, proliferation and/or differentiation to provide a therapeutic benefit upon administration of the dimerizer drug.

Dosages of the DNA will depend on the choice of dimerizer/drug binding domain pair, signaling domain, signaling pathway, design of the DNA constructs, type of vector used, and route of administration, as well as on factors such as the severity of the condition being treated; the age, weight and condition of the mammal. Accepted therapeutically effective dosages of viral vectors for use on human subjects is generally in the range of about 20 to about 50 ml of saline solution containing from about $1 \times 10^7$ to $1 \times 10^{10}$ pfu/ml of viruses. Dosage decisions will typically be made by a patient's physician taking into account the foregoing factors. Effectiveness of the transfection or infection may be determined, if desired, by analysis, using conventional molecular biological techniques, of cells recovered from the recipient. If desired, the administration of DNA to the mammal may be repeated.

The fusion proteins, as previously mentioned, generally comprise at least one signaling domain and at least one drug-binding domain. The signaling domain comprises a polypeptide sequence which upon multimerization triggers a desired cellular signal, e.g., for growth, proliferation and/or differentiation. Typically, a signaling domain comprises at least the cytoplasmic portion of a receptor (or signaling subunit thereto) for a growth or differentiation factor. Such receptors include among others c-kit, gp130 and flt-3; a receptor for a colony stimulating factor such as G-CSF, CSF-1, thrombopoietin or erythropoietin; or a receptor for another protein hormone such as growth hormone, EGF, prolactin, hepatocyte growth factor or a neurotrophic factor such as neurotrophin-3 or bFGF or other signaling molecules such as thyroid hormone T3 or T3/T4, ciliary neurotrophic factor, PDGF or IGF-1, which help illustrate this set.

In addition to the signaling domain, the fusion protein contains at least one protein domain which binds to a drug permitting drug-induced protein dimerization. Drug-binding domains encompass protein domains which are capable of binding to a ligand or dimerizer drug, as in the case, e.g., of an FKBP domain and the drug, FK506, discussed below. Drug-binding domains further encompass protein domains which are capable of binding to a complex of the drug with another binding protein, as in the case of the FRB domain of FRAP which binds to the rapamycin:FKBP complex. Examples of pairs of receptor domains and drugs which are known in the art and have been demonstrated to be effective in such regulated transcription systems, and which may be used in the practice of the subject invention, include FKBP/FK1012, FKBP/synthetic divalent FKBP ligands (see WO 96/06097 and WO 97/31898), FRB/rapamycin:FKBP (see, e.g., WO 96/41865 and Rivera, et al. *Nature Medicine* 2:1028, 1997), cyclophilin/cyclosporin (see, e.g., WO 94/18317), DHFR/methotrexate (see, e.g., Licitra, et al. *Proc. Natl. Acad. Sci. USA* 93:12817, 1996) and DNA gyrase/coumermycin (see, e.g., Farrar, et al. *Nature* 383:178, 1996). Currently preferred embodiments involve the use of binding domains derived from immunophilin, cyclophilin and/or FRAP proteins.

The fusion proteins may further comprise a cellular localization domain such as a membrane retention domain. See, e.g., PCT/US94/01617, especially pages 26-27. Briefly, a nucleic acid encoding a membrane retention domain can be isolated from a cDNA encoding a membrane-bound protein, whether endogenous to the host cell or not. The membrane retention domain may be a transmembrane retention domain, i.e., an amino acid sequence which extends across the membrane as in the case of cell surface proteins, including many receptors. The transmembrane peptide sequence may be extended to span part or all of an extracellular and/or intracellular domain as well. Alternatively, the membrane retention domain may be a lipid membrane retention domain such as a myristoylation or palmitoylation site which permits association with the lipids of the cell surface membrane. Lipid membrane retention domains will usually be added at the 5' end of the coding sequence for N-terminal binding to the membrane and, proximal to the 3' end for C-terminal binding. Peptide sequences involving post-translational processing to provide for lipid membrane binding are described by Carr, et al. *Proc. Natl. Acad. Sci. USA* 79:6128, 1988; Aitken, et al. *FEBS Lett.* 150:314, 1982; Henderson, et al. *Proc. Natl. Acad. Sci. USA* 80:319, 1983; Schulz, et al. *Virology* 123:2131, 1984; Dellman, et al. *Nature* 314:374, 1985; and reviewed in *Ann. Rev. of Biochem.* 57:69, 1988. An amino acid sequence of interest includes the sequence MGSSKSKPKDPSQR [SEQ ID NO:1]. Various DNA sequences can be used to encode such sequences in the various fusion proteins of this invention. Other localization domains include organelle-targeting domains and sequences such as KDEL [SEQ ID NO:2] and HDEL [SEQ ID NO:3] which target proteins bearing them to the endoplasmic reticulum, as well as nuclear localization sequences. Various cellular localization sequences and signals are well-known in the art.

Fusion proteins of this invention comprise a drug binding domain and one or more domains which are heterologous thereto and which typically comprise a signaling domain and/or a cellular localization domain.

The recombinant DNA constructs of this invention typically comprise a coding sequence encoding the desired fusion protein operably linked to one or more expression control elements including such elements as a promoter, enhancer, ribosome binding site, etc., such that the construct contains sufficient regulatory elements to direct the expression of the fusion protein in transduced cells.

As mentioned above, the drugs used for selection in the practice of this invention are not cytotoxic. In fact, a drug used in the practice of this invention preferably has substantially no pharmacologic activity other than the activity triggered by multimerization of fusion proteins containing at least one drug binding domain. By that we mean that the effects observed following treatment of cells with drug are significantly greater, by any scientifically valid measurement, in the case of cells engineered to express fusion proteins containing at least one drug binding domain, e.g., as provided herein, as compared to non-engineered cells. Preferably the drug is a synthetic compound which does not occur in nature. Preferably it binds to a fusion protein of this invention with an affinity at least $10^2$ and more preferably at least $10^3$ greater than its affinity for a protein naturally occurring in the host cells. Furthermore, unlike hormones such as estrogen or related compounds such as estradiol, the drug should have no significant pharmacologic activities on cells or on mammals which have not been engineered to express drug-binding fusion proteins. Said differently, the preferred drugs for use in the practice of this invention, and to which the preferred fusion proteins bind, have substantially no pharmacologic activity on normal, naturally occurring, i.e., non-engineered, mammalian cells.

The drug is preferably a "small-molecule" drug, meaning that it is not a protein (e.g., it is not an antibody, cytokine or growth factor protein); it has a molecular weight of less than about 5 kD, preferably less than about 3 kD, and more preferably less than about 2 kD; and/or is cell permeant. In preferred embodiments of the invention, the drug is multivalent and binds to two or more fusion protein molecules, in effect, crosslinking the fusion proteins by interactions with a drug-binding domain on each of two or more fusion protein molecules.

Based on the design principles disclosed herein, a number of potentially significant new methods and materials are thus provided.

As one object of this invention, a method is provided for rendering a subpopulation of primary mammalian cells susceptible to drug-induced growth, proliferation or differentiation, as has been alluded to above.

As another object of the invention, a method is provided for expanding a subpopulation of mammalian cells. The method involves providing a subpopulation of genetically engineered mammalian cells (as mentioned above and disclosed in further detail below) and treating that subpopulation of cells with an appropriate dimerizing drug. The genetically engineered mammalian cells contain at least one recombinant DNA construct encoding a specialized fusion protein. In each of the various embodiments of the invention, the fusion proteins typically (a) comprise at least one signaling domain and at least one drug-binding domain (to which the drug binds), and (b) induce growth, proliferation and/or differentiation upon multimerization with one or more other fusion protein molecules containing at least one signaling domain. Preferably the cells are primary cells and may be selected from a variety of tissue types, including hemopoietic cells, embryonic stem cells (Thomson, et al. *Science* 282:1145, 1998), hepatic cells, muscle cells, nerve cells, mesenchymal cells, cartilage and/or bone cells, intestinal cells, pancreatic cells or kidney cells, or a subpopulation of cells obtained therefrom; the fusion protein binds to a selected drug which is not a protein, has a molecular weight less than 5 kD, and/or is cell-permeant; the drug is multivalent to permit cross-linked multimers comprising two or more molecules of the fusion protein(s); and, exposure of the transduced cells to the drug induces the growth, proliferation and/or differentiation of cells. Again, the cells may have been transduced with the recombinant DNA construct(s) ex vivo or in vivo, and the transduced cells may be treated with dimerizing drug ex vivo and/or in vivo.

As another object of the invention, a method is provided for treating a disease or pathological condition in a mammal involving administration of an expanded subpopulation of cells, e.g., hemopoietic cells such as megakaryocytes or neutrophils, to the mammal.

As another object of the invention, methods are provided for rendering a mammal susceptible to drug-mediated expansion of a subpopulation of cells for the treatment of a disease or pathological condition. One method involves transducing cells in the mammal with one or more DNA constructs encoding a fusion protein of this invention. An alternative method involves transducing such cells ex vivo and then introducing the transduced cells into the mammal.

As another object of the invention, a method is provided for treating a disease or pathological condition in a mammal which is susceptible to drug-mediated expansion of a subpopulation of cells. The method involves administration of a dimerizing agent to the mammal to induce growth, proliferation and/or differentiation of a subpopulation of cells, e.g., hemopoietic cells such as megakaryocytes or neutrophils, to the mammal.

This invention also provides a subpopulation of primary cells which have been genetically engineered to grow, proliferate or differentiate upon the addition of dimerizer. These cells contain the dimerizer dependent signaling constructs, and may further contain an additional heterologous gene, for example, one that is capable of correcting a genetic defect.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Definitions

Figure 1A:
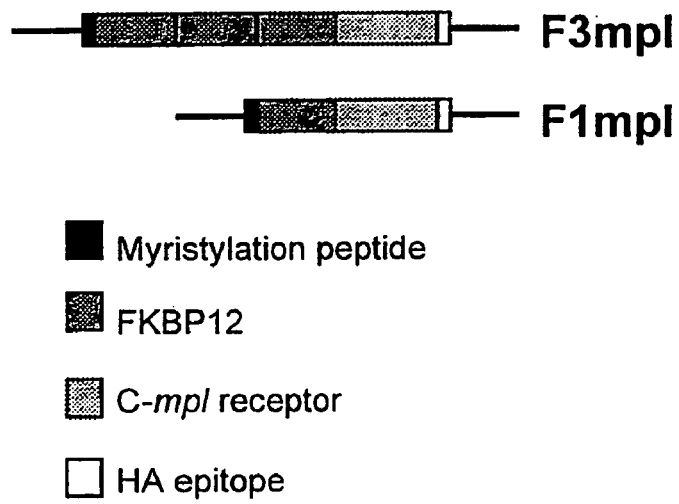
FIG. 1: Test of constructs. (A) Schematic design. An XhoI-linkered fragment encoding the intracellular domain of mpl was PCR amplified using Pfu polymerase and the following primer pairs: 5'GGC TCG AGA AGT GGC AAT TTC CTG CG3' [SEQ ID NO:4] and 5'GGC TCG AGG GGC TGC TGC CAA TAG C3'[SEQ ID NO:5]. Following sequence confirmation, the XhoI digested fragment was inserted into the SalI site of the construct F3 (Blau, et al. *Proc. Natl. Acad. Sci. USA* 92:9805, 1997) to produce F3mpl. F3mpl contains a myristoylation domain to direct localization to the inner surface of the cell membrane, three copies of the FK506-binding peptide FKBP12, the intracellular portion of mpl and an HA epitope tag to permit detection of the fusion protein by Western assay. F1mpl differs from F3mpl in that it contains only a single FKBP12 site. These constructs were used to generate Ba/F3 clones expressing high levels of the fusion protein as described previously (Blau, et al. *Proc. Natl. Acad. Sci. USA*, 1997). (B) Cell proliferation (3-[4,5-dimethylthiazol-2-yl]-2,5-diphenyltetrazolium bromide—MTT) assays for transfected Ba/F3 cell clones expressing either F3mpl (closed symbols) or F1mpl (open circles) were performed as described previously (Blau, et al. *Proc. Natl. Acad. Sci. USA*, 1997). Peak proliferative responses were observed at a concentration of 100 nM FK1012. (C) MTT assays for retrovirally transduced Ba/F3 cell clones expressing F1mpl driven by MSCVneo. Results, plotted as a fraction of the $OD_{570}$-630 obtained in the same clones using 5% IL3-containing WEHI conditioned medium, denote the mean of three experiments. Error bars denote standard deviations.

The definitions and orienting information below will be helpful for a full understanding of this document.

The terms "protein," "polypeptide" and "peptide" are used interchangeably herein.

"DNA constructs," as that term is used herein, denote DNA molecules used in the practice of this invention which are generally recombinant, as that term is defined below, and which may exist in free form (i.e., not covalently linked to additional DNA) or may be present within a larger DNA molecule such as a DNA vector or a chromosome of a genetically engineered host cell. DNA constructs of particular interest are those which encode fusion proteins of this invention. The DNA construct may further include one or more of the following DNA elements relevant to regulation of transcription, translation, and/or other processing of the coding region or gene product thereof transcriptional promoter and/or enhancer sequences, a ribosome binding site, introns, etc.

"Recombinant," "chimeric" and "fusion," as those terms are used herein, denote materials comprising various component domains, sequences or other components which are mutually heterologous in the sense that they do not occur together in the same arrangement, in nature. More specifically, the component portions are not found in the same continuous polypeptide or nucleotide sequence or molecule in nature, at least not in the same cells or order or orientation or with the same spacing present in the chimeric protein or recombinant DNA molecule of this invention.

"Dimerization," "oligomerization" and "multimerization" are used interchangeably herein and refer to the association or clustering of two or more protein molecules, mediated by the binding of a drug to at least one of the proteins. In preferred embodiments, the multimerization is mediated by the binding of two or more such protein molecules to a common divalent or multivalent drug. The formation of a complex comprising two or more protein molecules, each of which containing one or more FKBP domains, together with one or more molecules of an FKBP ligand which is at least divalent (e.g., FK1012, AP1510 AP1903 or AP20187) is an example of such association or clustering. In cases where at least one of the proteins contains more than one drug binding domain, e.g., where at least one of the proteins contains three FKBP domains, the presence of a divalent drug leads to the clustering of more than two protein molecules. Embodiments in which the drug is more than divalent (e.g., trivalent) in its ability to bind to proteins bearing drug binding domains also can result in clustering of more than two protein molecules. The formation of a tripartite complex comprising a protein containing at least one FRB domain, a protein containing at least one FKBP domain and a molecule of rapamycin is another example of such protein clustering. In certain embodiments of this invention, fusion proteins contain multiple FRB and/or FKBP domains. Complexes of such proteins may contain more than one molecule of rapamycin or a derivative thereof or other dimerizing agent and more than one copy of one or more of the constituent proteins. Again, such multimeric complexes are still referred to herein as tripartite complexes to indicate the presence of the three types of constituent molecules, even if one or more are represented by multiple copies. The formation of complexes containing at least one divalent drug and at least two protein molecules, each of which contains at least one drug binding domain, may be referred to as "oligomerization" or "multimerization," or simply as "dimerization," "clustering" or association."

"Dimerizer" denotes a drug which brings together two or more proteins in a multimeric complex.

"Divalent," as that term is applied to drugs in this document, denotes a drug which is at least divalent with respect to proteins containing a receptor domain which binds to the drug. Said differently, a divalent drug is capable of complexing with at least two protein molecules which contain drug binding domains, effectively cross-linking the proteins to form a three (or greater number)-component complex. "Divalent" and "multivalent" are used interchangeably herein.

"Genetically engineered cells" denotes cells which have been modified ("transduced") by the introduction of recombinant or heterologous nucleic acids (e.g., one or more DNA constructs or their RNA counterparts) and further includes the progeny of such cells which retain part or all of such genetic modification.

"Primary cells," as the term is used herein, refers to all cells obtained from a mammal excluding those that have been transformed or otherwise irreversibly immortalized. Specifically included under this definition are human embryonic stem cells (Thomson, et al. *Science* 282:1145, 1998).

"Transduction" and "transducing" refer to any manner of delivery of nucleic acids into cells, including, but not limited to, transformation, transfection, electroporation and infection.

As used herein, the term "cellular composition" refers to a preparation of cells, which preparation may include, in addition to the cells, non-cellular components such as cell culture media, e.g., proteins, amino acids, nucleic acids, nucleotides, co-enzyme, anti-oxidants, metals and the like. Furthermore, the cellular composition can have components which do not affect the growth or viability of the cellular component, but which are used to provide the cells in a particular format, e.g., as polymeric matrix for encapsulation or a pharmaceutical preparation.

The term "differentiation," as used herein, refers to an alteration in the pattern of gene expression in cells which typically is associated with one or more of the following: changes in morphology, lineage (see below), motility, adhesion, cell cycle regulation, etc.

The term "lineage committed cell" refers to a stem cell that is no longer pluripotent but has become restricted to a specific lineage, e.g., in the case of hematopoietic stem cells, a myeloid, lymphoid, erythroid lineage. The lineage committed cell subsequently differentiates to specialized cell types, e.g., in the case of hematopoietic lineage committed cells, to cell types such as erythrocytes, T and B lymphocytes.

The term "stem cell" refers to an undifferentiated cell which is capable of self-renewal, i.e., proliferation to give rise to more stem cells, and may give rise to lineage committed progenitors which are capable of differentiation and expansion into a specific lineage. In a preferred embodiment, the term "stem cell" refers to a generalized mother cell whose descendants (progeny) specialize, often in different directions, by differentiation, e.g., by acquiring completely individual characters, as occurs in progressive diversification of embryonic cells and tissues. As used herein, the term "stem cells" refers generally to embryonic, hemopoietic and other stem cells of mammalian, e.g., human, origin. Hemopoietic stem cells are discussed below. By way of further example, a neuroepithlial stem cell composition can be expanded into various lineage-restricted precursor cells, including, e.g., neuron-restricted precursor cells and glial restricted precursor cells, which give rise respectively to neurons and to oligodendrocytes and type 1 and type 2 astrocytes. Human embryonic stem cells can be expanded into all three embryonic germ layers including gut epithelium (endoderm), cartilage, bone, smooth muscle, and striated muscle (mesoderm), and neural epithelium, embryonic ganglia, and stratified squamous epithelium (ectoderm).

A "stem cell composition" comprises a population of stem cells which can be maintained in culture for extended periods of time (e.g., days or weeks or more), which can be expanded by selection and transferred to secondary and higher order culture, and which is capable of differentiating into lineage committed cells, e.g., in the case of a hematopoietic stem cell composition, into cells of various lymphoid or myeloid lineages, particularly B and T lymphocytes, monocytes, macrophages, neutrophils, erythrocytes and the like.

A "hemopoietic stem cell" (HSC) refers to a population of cells capable of both self-renewal and differentiation into all defined hemopoietic lineages, i.e., myeloid, lymphoid or erythroid lineages; and inciting number of cells are capable of repopulating the hemopoietic system of a recipient who has undergone myeloablative treatment. HSCs can ultimately differentiate into "hemopoietic cells", including without limitation, common lymphoid progenitor cells, T cells (e.g., helper, cytotoxic, and suppressor cells), B cells, plasma cells, natural killer cells, common myeloid progenitor cells, monocytes, macrophages, mast cells, leukocytes, basophils, neutrophils, eosinophils, megakaryocytes, platelets, and erythroids. HSCs are identifiable by the presence of cell surface antigens of primitive phenotypes, e.g., CD34+Thy-1+Lin–, and negative staining for lineage-specific antigens.

A "disease of a hemopoietic cell" refers to any condition characterized by impairment of any normal function of a hemopoietic cell. Diseases of a hemopoietic cell that can be treated utilizing the methods and materials of the present invention include, without limitation, genetic disorders (e.g., Adenosine Deaminase Deficiency, Fanconi's Anemia, and hemoglobinopathies such as Sickle Cell Anemia, Thalassemias, and Hemoglobin C Disease), as well as diseases acquired by infectious or non-infectious means (e.g., Acquired Immune Deficiency Syndrome and leukemias).

A "therapeutically effective dose" of a drug denotes a treatment- or prophylaxis-effective dose, e.g., a dose which yields detectable proliferation of the genetically engineered cells or detectable generation (e.g., through differentiation and/or expansion) of a desired population of cells, or a dose which is predicted to be treatment- or prophylaxis-effective by extrapolation from data obtained in animal or cell culture models. A therapeutically effective dose is usually preferred for the treatment of a human or non-human mammal.

Dimerization-Based Regulation: Generally

As noted above, dimerization-based approaches using divalent drugs to crosslink specialized fusion proteins are preferred for regulating signaling in the practice of this invention. The general approach is broadly applicable to a wide variety of drugs and drug-binding domains, signaling domains, cell types to be transduced and overall objectives. A variety of components and design choices are available to the practitioner for addressing a set of objectives which are now accessible. The various elements are separately discussed below.

Signaling Domains

Signaling domains of this invention include, among others, receptor cytoplasmic domains, including domains comprising naturally occurring human peptide sequence, as well as fragments, subunits and analogs of the foregoing which retain one or more of the characteristic biological activities of the parent protein, e.g., induction of cellular growth, proliferation and/or differentiation. When this invention is applied to human patients, it is preferred that the signaling domain comprise a naturally occurring human peptide sequence.

Preferred fusion proteins of this invention contain a cytoplasmic domain from one of the various cell surface membrane receptors, including mutants thereof, wherein activation of the receptor induces cellular proliferation. The receptor-associated cytoplasmic domains of particular interest will have the following characteristics: genes which are activated other than those which induce mitogenesis will not affect the intended purpose for which these cells are to be used; the cells in which the signaling is induced will contain all the factors necessary for response to the fusion protein; oligomerization of the cytoplasmic domain results in signal initiation; and joining of the cytoplasmic domain to a desired drug-binding domain will not interfere with signaling. A number of different cytoplasmic domains are known. Many of these domains are tyrosine kinases or are found completed or otherwise associated with tyrosine kinases. For a review see Cantley, et al. (*Cell* 64:281, 1991). Tyrosine kinase receptors which are activated by cross-linking, e.g., dimerization (based on nomenclature first proposed by Yarden and Ulrich (*Annu. Rev. Biochem.* 57:443, 1988) include subclass I: EGF-R, ATR2/neu, HER2/neu, HER3/c-erbB-3, Xmrk; subclass II: insulin-R, IGF-1-R [insulin-like growth factor receptor], IRR; subclass III: PDGF-R-A, PDGF-R-B, CSF-1-R (M-CSF/c-Fms), c-kit, fit-3, STK-1/Flk-2; and subclass IV: FGF-R, fig [acidic FGF], bek [basic FGF]); neurotrophic tryosine kinases: Trk family, includes NGF-R, Ror1,2. Receptors which associate with tyrosine kinases upon cross-linking include the CD3 ζ-family: CD3 ζ and CD3 η (found primarily in T cells, associates with Fyn); β and β chains of Fee RI (found primarily in mast cells and basophils); γ chain of Fcγ RIII/CD16 (found primarily in macrophages, neutrophils and natural killer cells); CD3 γ, -δ, and -ε (found primarily in T cells); Ig-α/MB-1 and Ig-β/B29 (found primarily in B cell). Many cytokine and growth factor receptors associate with common β subunits which interact with tyrosine kinases and/or other signaling molecules and which can be used as cytoplasmic domains in chimeric proteins of this invention. These include (1) the common β subunit shared by the GM-CSF, IL-3 and IL-5 receptors; (2) the β chain gp130 associated with the IL-6, leukemia inhibitory factor (LIF), ciliary neurotrophic factor (CNTF), oncostatin M, and IL-11 receptors; (3) the IL-2 receptor γ subunit associated also with receptors for IL-4, IL-7 and IL-13 (and possibly IL-9); and (4) the β chain of the IL-2 receptor which is homologous to the cytoplasmic domain of the G-CSF receptor.

The interferon family of receptors which include interferons α/β and γ (which can activate one or more members of the JAK, Tyk family of tyrosine kinases) as well as the receptors for growth-hormone; hepatocyte-growth factor, thrombopoietin, erythropoietin and prolactin can also be used as sources for cytoplasmic domains. However, any molecule that stimulates cell growth, proliferation and/or differentiation upon homodimerization, clustering, etc., may be used in the practice of this invention. For example, one could use a key downstream signaling molecule which is not a receptor, e.g., JAK2, which is capable of stimulating cell proliferation upon homodimerization, as has been shown in the case of TEL-JAK2 fusion proteins (Lacronique, et al. *Science* 278:1309-1312, 1997).

As mentioned above, fusion proteins of this invention can be targeted to the membrane if so desired, by incorporating a myristoylation sequence, e.g., from c-src, or any other membrane targeting or anchoring sequence into the fusion protein's design.

The signaling domain, as it exists naturally or as it may be truncated, modified or mutated, will be at least about 10, usually at least about 30 amino acids, more usually at least about 50 amino acids, and generally not more than about 400 amino acids, usually not more than about 200 amino acids. (See Romeo, et al. *Cell* 68:889, 1992) While any species can be employed, the species endogenous to the host cell is usually preferred. However, in many cases, a signaling domain from a different species can be used effectively. Any of the above indicated signaling domains may be used, as well as others which are presently known or may subsequently be discovered.

Furthermore, one may use several signaling domains in combination, such as the receptors for EPO and mpl, to create novel composite signaling domains. Alternatively, for a receptor which requires more than a single chain for signaling, such as the IL-2 receptor, one may use a construct in which the component chains are fused together. One may also provide the cells with more than one chimeric protein, each of which binds a different drug. For example, one can introduce constructs encoding a first fusion protein containing at least one FRB domain and an flt-3 domain and a second fusion protein containing at least one FKBP domain and a c-kit domain. In these cells, the c-kit containing proteins would homodimerize upon addition of FK1012, while the c-kit and flt-3 proteins would heterodimerize upon the addition of rapamycin. In a similar approach, one might introduce DNA encoding a "daisy chain" of two or more drug binding domains targeted to the membrane using, e.g., a myristoylation site. Along with this construct, any number of constructs encoding different drug-binding domain/signaling domain fusions can be introduced. Using this approach, a multiplicity of proliferative responses could be achieved upon treatment with one or more drugs.

Drug Binding Domains

The drug binding domain of a fusion protein of this invention can be any protein domain for which a ligand is known or can be identified. The binding domain can be internal or external to the cellular membrane, depending upon the nature of the construct and the choice of drug. A wide variety of binding proteins, including receptors, are known, including binding proteins associated with the cytoplasmic regions indicated above. Of particular interest are binding proteins for which ligands (preferably small organic ligands) are known or may be readily produced. These receptors or drug binding domains include the FKBPs and cyclophilin receptors, the tetracycline receptor, and the like, as well as "unnatural" receptors, which can be obtained from antibodies, particularly the heavy or light chain subunit, mutated sequences thereof, random amino acid sequences obtained by stochastic procedures, combinatorial syntheses, and the like. For the most part, the receptor domains will be at least about 50 amino acids, and fewer than about 350 amino acids, usually fewer than 200 amino adds, either as the natural domain or truncated active portion thereof. Preferably the binding domain will be small (<25 kD, to allow efficient transfection in viral vectors), monomeric (unlike the avidin-biotin system), nonimmunogenic, and should have synthetically accessible, cell permeable, nontoxic ligands that can be configured for dimerization. Also preferably, the drug binding domain will not bind appreciably to any endogenous ligands, but will bind only to the small molecule drug provided in the practice of this invention.

The ability to employ in vitro mutagenesis or combinatorial modifications of sequences encoding proteins allows for the production of libraries of proteins which can be screened for binding affinity for different ligands. For example, one can totally randomize a sequence of 1 to 5, 10 or more codons, at one or more sites in a DNA sequence encoding a binding protein, make an expression construct and introduce the expression construct into a unicellular microorganism, and develop a library. One can then screen the library for binding affinity to one or desirably a plurality of ligands. The best affinity sequences which are compatible with the cells into which they would be introduced can then be used as the binding domain. The ligand may be screened with the host cells to be used to determine the level of binding of the ligand to endogenous proteins. A binding profile may be defined weighting the ratio of binding affinity to the mutagenized binding domain with the binding affinity to endogenous proteins. Those ligands which have the best binding profile could then be used as the ligand. Phage display techniques, as a non-limiting example, can be used in carrying out the foregoing.

For dimerization-based approaches to regulation of cellular functions in human subjects, the use of fusion proteins which contain protein domains of human origin, or derivatives thereof, are preferred. Currently preferred drug binding domains are based on FKBP12, and in some cases, the FRB domain of FRAP. Those domains can be engineered to recognize novel FKBP ligands and/or rapamycin derivatives, e.g., as disclosed in PCT/US94/01617 and PCT/US96/09948 (WO 96/41865).

Thus, depending on design preferences of the practitioner, a wide variety of drugs may be used. In general, drugs for use in this invention are preferably non-proteinaceous and preferably have a molecular weight below about 5 kD, more preferably below about 3 kD. FK1012, cyclosporin-based divalent ligands, fujisporin and related types of semisynthetic ligands are disclosed in WO 94/18317 and PCT/US94/08008 (WO 95/02694). Drugs based on synthetic FKBP ligand monomers are disclosed in WO 96/06097 and WO 97/31898, and drugs based on rapamycin and derivatives are disclosed in WO 96/41865. Other ligands are disclosed in various cited references, including those cited and discussed above.

All of the foregoing components may be used in the practice of this invention and the full contents of the various documents referred to above are incorporated herein by reference. Those documents also provide guidance in the design of constructs encoding such chimeras, expression vectors containing them, design and use of suitable target gene constructs, and their use in engineering host cells. As further guidance in that regard, specific examples are provided below which illustrate the design, construction and use of constructs for the regulated expression of target genes using dimerization of signal transduction domains.

FKBP, FRB, cyclophilin and other drug binding domains comprising naturally occurring peptide sequence may be used in the design of fusion proteins for use in practicing this invention. Alternatively, domains derived from naturally occurring sequences but containing one or more mutations in peptide sequence, generally at up to 10 amino acid positions, and preferably at 1-5 positions, more preferably at 1-3 positions and in some cases at a single amino acid residue, may be used in place of the naturally occurring counterpart sequence and can confer a number of important features. This is described at length in the previously cited patent documents, together with numerous examples of such mutations and corresponding ligands, all of which are incorporated at this point specifically in that regard.

For example, illustrative mutations of current-interest in FKBP domains include the following:

TABLE 1

| F36A | Y26V | F46A | W59A |
| F36V | Y26S | F48H | H87W |
| F36M | D37A | F48L | H87R |
| F36S | I90A | F48A | F36V/F99A |
| F99A | I91A | E54A | F36V/F99G |
| F99G | F46H | E54K | F36M/F99A |
| Y26A | F46L | V55A | F36M/F99G |

Note that the entries in TABLE 1 identify the native amino acid by single letter code and sequence position, followed by the replacement amino acid in the mutant. Thus, F36V designates a human FKBP12 sequence in which phenylalanine at position 36 is replaced by valine. F36V/F99A indicates a double mutation in which phenylalanine at positions 36 and 99 are replaced by valine and alanine, respectively.

Illustrative FRB mutations, especially for use with rapamycin analogs bearing substituents other than —OMe at the C7 position include amino acid substitutions for one or more of the residues Tyr2038, Phe2039, Thr2098, Gln2099, Trp2101 and Asp2102. Exemplary mutations include Y2038H, Y2038L, Y2038V, Y2038A, F2039H, F2039L, F2039A, F2039V, D2102A, T2098A, T2098N, and T2098S. Rapamycin derivatives bearing substituents other than —OH at C28 and/or substituents other than =O at C30 may be used to obtain preferential binding to FRAP proteins bearing an amino acid substitution for Glu2032. Exemplary mutations include E2032A and E2032S. Peptide sequence numbering and rapamycin numbering is with reference to WO 96/41865.

Illustrative mutations in cyclophilin domains (and corresponding cyclosporin compounds) are disclosed in WO 94/18317 and may also be adapted for use in practicing the subject invention.

Design and Assembly of the DNA Constructs

Constructs may be designed in accordance with the principles, illustrative examples and materials and methods disclosed in the patent documents and scientific literature cited herein, each of which is incorporated herein by reference, with modifications and further exemplification as described herein. Components of the constructs can be prepared in conventional ways, where the coding sequences and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair;" ligation, in vitro mutagenesis, etc., as appropriate. In the case of DNA constructs encoding fusion proteins, DNA sequences encoding individual domains and sub-domains are joined such that they constitute a single open reading frame encoding a fusion protein capable of being translated in cells or cell lysates into a single polypeptide harboring all component domains. The DNA construct encoding the fusion protein may then be placed into a vector that directs the expression of the protein in the appropriate cell type(s). For biochemical analysis of the encoded chimera, it may be desirable to construct plasmids that direct the expression of the protein in bacteria or in reticulocyte-lysate systems. For use in the production of proteins in mammalian cells, the protein-encoding sequence is introduced into an expression vector that directs expression in these cells. Expression vectors suitable for such uses are well-known in the art. Various sorts of such vectors are commercially available.

Delivery of DNA: Ex Vivo and In Vivo

Any means for the introduction of heterologous DNA into mammalian cells, human or non-human, may be adapted to the practice of this invention. For the purpose of this discussion, the various DNA constructs described herein may together be referred to as the transgene. Ex vivo approaches for delivery of DNA include calcium phosphate precipitation, electroporation, lipofection and infection via viral vectors. Two general in vivo gene therapy approaches include (a) the delivery of "naked", lipid-complexed or liposome-formulated or otherwise formulated DNA and (b) the delivery of the heterologous DNA via viral vectors. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Feigner, et al. *Ann NY Acad. Sci* 126, 1995). Formulation of DNA, e.g., with various lipid or liposome materials, may then be effected using known methods and materials and delivered to the recipient mammal.

While various viral vectors may be used in the practice of this invention, retroviral-, AAV- and adenovirus-based approaches are of particular interest. See, for example, Dubensky, et al. *Proc. Natl. Acad. Sci. USA* 81:7529, 1984; Kaneda, et al. *Science* 243:375, 1989; Hebert, et al. *Proc. Natl. Acad. Sci. USA* 86:3594, 1989; Hatzoglu, et al. *J. Biol. Chem.* 265:17285, 1990 and Ferry, et al. *Proc. Natl. Acad Sci.*

USA 88:8377, 1991. The following additional guidance on the choice and use of viral vectors may be helpful to the practitioner.

Retroviral Vectors

Retroviruses are a class of RNA viruses in which the RNA genome is reversely transcribed to DNA in the infected cell. The retroviral genome can integrate into the host cell genome and requires three viral genes, gag, pol and env, as well as the viral long terminal repeats (LTRs). The LTRs also act as enhancers and promoters for the viral genes. The packaging sequence of the virus, ($\Psi$) allows the viral RNA to be distinguished from other RNAs in the cell (Verma, et al. *Nature* 389:239, 1997). For expression of a foreign gene, the viral proteins are replaced with the gene of interest in the viral vector, which is then transfected into a packaging line containing the viral packaging components. Packaged virus is secreted from the packaging line into the culture medium, which can then be used to infect cells in culture. Since retroviruses are unable to infect non-dividing cells, they have been used primarily for ex vivo gene therapy.

AAV Vectors

Adeno-associated virus (AAV)-based vectors are of general interest as a delivery vehicle to various tissues, including muscle and lung. AAV vectors infect cells and stably integrate into the cellular genome with high frequency. AAV can infect and integrate into growth-arrested cells (such as the pulmonary epithelium), and is non-pathogenic.

The AAV-based expression vector to be used typically includes the 145 nucleotide AAV inverted terminal repeats (flits) flanking a restriction site that can be used for subcloning of the transgene, either directly using the restriction site available, or by excision of the transgene with restriction enzymes followed by blunting of the ends, ligation of appropriate DNA linkers, restriction digestion, and ligation into the site between the ITRs. The capacity of AAV vectors is about 4.4 kb. The following proteins have been expressed using various AAV-based vectors, and a variety of promoter/enhancers: neomycin phosphotransferase, chloramphenicol acetyl transferase, Fanconi's anemia gene, cystic fibrosis transmembrane conductance regulator, and granulocyte macrophage colony-stimulating factor (see Table 1 in Kotin, *Human Gene Therapy* 5:793, 1994). A transgene incorporating the various DNA constructs of this invention can similarly be included in an AAV-based vector. As an alternative to inclusion of a constitutive promoter such as CMV to drive expression of the recombinant DNA encoding the fusion protein(s), an AAV promoter can be used (ITR itself or AAV p5 (Flotte, et al. *J. Biol. Chem.* 268:3781, 1993).

Such a vector can be packaged into AAV virions by reported methods. For example, a human cell line such as 293 can be co-transfected with the AAV-based expression vector and another plasmid containing open reading frames encoding AAV rep and cap under the control of endogenous AAV promoters or a heterologous promoter. In the absence of helper virus, the rep proteins Rep68 and Rep78 prevent accumulation of the replicative form, but upon superinfection with adenovirus or herpes virus, these proteins permit replication from the ITRs (present only in the construct containing the transgene) and expression of the viral capsid proteins. This system results in packaging of the transgene DNA into AAV virions (Carter, *Current Opinion in Biotechnology* 3:533, 1992; Kotin, *Human Gene Therapy* 5:793, 1994). Methods to improve the titer of AAV can also be used to express the transgene in an AAV virion. Such strategies include, but are not limited to: stable expression of the ITR-flanked transgene in a cell line followed by transfection with a second plasmid to direct viral packaging; use of a cell line that expresses AAV proteins inducibly, such as temperature-sensitive inducible expression or pharmacologically inducible expression. Additionally, one may increase the efficiency of AAV transduction by treating the cells with an agent that facilitates the conversion of the single stranded form to the double stranded form, as described in Wilson, et al. WO96/39530.

Concentration and purification of the virus can be achieved by reported methods such as banding in cesium chloride gradients, as was used for the initial report of AAV vector expression in vivo (Flotte, et al. *J. Biol. Chem.* 268:3781, 1993) or chromatographic purification, as described in O'Riordan, et al. WO97/08298.

For additional detailed guidance on AAV technology which may be useful in the practice of the subject invention, including methods and materials for the incorporation of a transgene, the propagation and purification of the recombinant AAV vector containing the transgene, and its use in transfecting cells and mammals, see e.g., Carter, et al. U.S. Pat. No. 4,797,368 (10 Jan. 1989); Muzyczka, et al. U.S. Pat. No. 5,139,941 (18 Aug. 1992); Lebkowski, et al. U.S. Pat. No. 5,173,414 (22 Dec. 1992); Srivastava, U.S. Pat. No. 5,252,479 (12 Oct. 1993); Lebkowski, et al. U.S. Pat. No. 5,354,678 (11 Oct. 1994); Shenk, et al. U.S. Pat. No. 5,436,146 (25 Jul. 1995); Chatterjee, et al. U.S. Pat. No. 5,454,935 (12 Dec. 1995), Carter, et al. WO 93/24641 (published 9 Dec. 1993), and Flotte, et al. U.S. Pat. No. 5,658,776 (19 Aug. 1997).

Adenovirus Vectors

Various adenovirus vectors have been shown to be of use in the transfer of genes to mammals, including humans. Replication-deficient adenovirus vectors have been used to express marker proteins and CFTR in the pulmonary epithelium. The first generation E1a deleted adenovirus vectors have been improved upon with a second generation that includes a temperature-sensitive E2a viral protein, designed to express less viral protein and thereby make the virally infected cell less of a target for the immune system (Goldman, et al. *Human Gene Therapy* 6:839, 1995). More recently, a viral vector deleted of all viral open reading frames has been reported (Fisher, et at *Virology* 217:11, 1996). Moreover, it has been shown that expression of viral IL-10 inhibits the immune response to adenoviral antigen (Qin, et al. *Human Gene Therapy* 8:1365, 1997).

DNA sequences of a number of adenovirus types are available from Genbank. The adenovirus DNA sequences may be obtained from any of the 41 human adenovirus types currently identified. Various adenovirus strains are available from the American Type Culture Collection, Rockville, Md., or by request from a number of commercial and academic sources. A transgene as described herein may be incorporated into any adenoviral vector and delivery protocol, by the same methods (restriction digest, linker ligation or filling in of ends, and ligation) used to insert the CFTR or other genes into the vectors. Hybrid Adenovirus-AAV vectors represented by an adenovirus capsid containing selected portions of the adenovirus sequence, 5' and 3' AAV ITR sequences flanking the transgene and other conventional vector regulatory elements may also be used. See e.g., Wilson, et al. International Patent Application Publication No. WO 96/13598. For additional detailed guidance on adenovirus and hybrid adenovirus-AAV technology which may be useful in the practice of the subject invention, including methods and materials for the incorporation of a transgene, the propagation and purification of recombinant virus containing the transgene, and its use in transfecting cells and mammals, see also Wilson et al. WO 94/28938, WO 96/13597 and WO 96/26285, and references cited therein.

Generally, the DNA or viral particles are transferred to a biologically compatible solution or pharmaceutically acceptable delivery vehicle, such as sterile saline, or other aqueous or non-aqueous isotonic sterile injection solutions or suspensions, numerous examples of which are well-known in the art, including Ringer's, phosphate buffered saline, or other similar vehicles.

Preferably, the DNA or recombinant virus is administered in sufficient amounts to transfect cells at a level providing therapeutic benefit without undue adverse effects. Optimal dosages of DNA or virus depends on a variety of factors, as discussed previously, and may thus vary somewhat from patient to patient. Again, therapeutically effective doses of viruses are considered to be in the range of about 20 to about 50 ml of saline solution containing concentrations of from about $1 \times 10^7$ to about $1 \times 10^{10}$ pfu of virus/ml, e.g., from $1 \times 10^8$ to $1 \times 10^9$ pfu of virus/ml.

Cells

Any cell type may be used in the practice of this invention, as long as it can be engineered to express the fusion proteins and induced to grow, proliferate and/or differentiate upon addition of dimerizer. These include, among others, cells obtained from embryonic, juvenile or adult mammals, including stem cells, progenitor cells and precursor cells of various types and tissues. A variety of such cells and methods for obtaining and handling them are known in the art. By way of non-limiting example, such cells include stem cells, progenitor cells and precursor cells from bone marrow, peripheral blood, cord blood or fetal liver (e.g., hemopoietic stem cells and lymphoid, myeloid and erythroid precursor cells) and from neural tissue (e.g., neuroepithlial stem cells and neuron-restricted and glial-restricted precursor cells; see, e.g., Mayer-Proschel, et al. *Journal of NIH Research* 9:31, 1997 and references cited therein). In another nonlimiting example, human embryonic stem cells (ES) could be used (see Thomson, et al. *Science* 282:1145, 1998). In particular, this invention could be used either to expand human ES cells or to induce their differentiation toward desired cell lineages through the use of appropriate signaling domains. Other cells for use in practicing this invention include, for example, lymphocytes, liver cells (hepatocytes, Kupfer cells, biliary tract cells), keratinocytes, fibroblasts, nerve cells, skeletal, smooth and cardiac muscle cells, osteoblasts, osteoclasts, intestinal cells, pulmonary bronchial epithelial cells, pancreatic islet cells, adrenal cells, vascular endothelial cells, pituitary cells, basal ganglia cells and mesenchymal cells. Genetic engineering of stem cells and/or various progenitor and/or precursor cells is of particular interest.

By way of illustration, hemopoietic stem, multipotential progenitor or precursor cells can be obtained from the bone marrow, peripheral blood, cord blood and fetal liver. For instance, such cells may be obtained from the peripheral blood either during basal conditions or soon after the administration of chemotherapy, growth factors or antibodies that result in the redistribution of early hemopoietic cells from the bone marrow into the peripheral blood. Commercially available methods of cell purification can be used to enrich for specific cell populations of interest. Hemopoietic stem cells and multipotential progenitors can be enriched through the selection of cells bearing CD34, c-kit, flt-3, AC133, other surface membrane molecules, or other phenotypic properties based on size or buoyant density. Similarly, specific cell lineages can be enriched using other surface membrane molecules. For example, lymphocyte populations can be enriched through the use of antibodies directed against CD3, CD4, CD5, CD8, CD19, CD20 and other molecules. Erythroid cell populations can be enriched using antibodies directed against the transferrin receptor, Ter119, the erythropoietin receptor, or other molecules. Myeloid populations can be enriched through the presence of CD33, CD18, CD11b, or other molecules. Megakaryocytic populations can be enriched through selection based on the presence of mpl, gpIIbIIIa, gpIb/IX, or other molecules. Other types of stem, multipotential progenitor and precursor cells may be obtained by methods known in the art.

Uses

Genetically engineered cells produced as described herein may be used as research tools. Generally, primary cells do not survive in culture for more than a few passages. Such primary cells may be immortalized by the introduction of viral genes and/or oncogenes, but those cells are often both genotypically and phenotypically altered by the expression of the oncogene. Moreover, the cells are immortalized irreversibly. In contrast, this invention provides methods for reversible expansion of genetically engineered cells for use, among other things, in research. It should also be noted that when targeting a heterogeneous population of cells such as bone marrow, previously unidentified cell types may be selectively expanded and identified. Thus, by carrying out the steps of genetically engineering cells within a heterogeneous population, and thereby producing engineered cells comprising a dimerizer-dependent signaling apparatus, then observing the cell type(s) which are expanded following exposure of the cells to the dimerizer, one can identify the cell type(s) which is/are responsive to the signaling pathway triggered by the dimerized signaling domains.

Cells produced ex vivo by the methods of this invention may also be used for therapeutic purposes, e.g., transplantation. Thus, cells of any type may be harvested from a donor mammal and transduced to express the fusion proteins described herein. The cells can then be treated with dimerizer, which will allow the transduced cells to grow, proliferate and/or differentiate while non-transduced cells will grow at their basal rate. When the population of the cells of interest has expanded to the desired size it can be introduced into a mammalian, preferably human, recipient. Alternatively, the transduced cells can be introduced into the recipient mammal and then expanded in vivo by administration of the dimerizer drug to the recipient mammal. The donor and recipient mammal may be the same individual, that is, the transplant may be autologous. Cells expanded by the methods of this invention may be used for transplantation of any tissue type, including bone marrow, heart, liver, pancreas, lung, kidney, skin, intestine, CNS and other tissues. An alternative approach would be to transduce human ES cells to express one or more of the fusion proteins described herein. These cells could then be treated with dimerizer, resulting either in their proliferation or differentiation toward the desired cell lineage.

The ability to expand hematopoietic stem cells, perhaps in unlimited quantities, has major applications for cancer chemotherapy as well as bone marrow transplantation ("BMT"). The National Bone Marrow Donor Registry now has over 2,000,000 participants. Donors are still not identified for about 30% of patients who need a BMT. When donors are identified, they undergo an extensive medical history and physical examination and then undergo bone marrow harvest (a painful procedure) under general anesthesia. While peripheral blood stem cell harvest is currently expected to replace traditional bone marrow harvest, the donor will still have to receive a drug (GCSF) which causes side effects such as bone pain and headache. Following stem cell harvest, the cells are escorted by a doctor or nurse to the site of the recipient (who can be on another continent). The average time between identification of a donor and the BMT procedure is three to four months. Many patients have diseases that do not permit this long of a delay. The advantages of banked, dimerizer expanded stem cells would be profound. One could expand stem cells dramatically, perhaps to unlimited quantities, for use by any number of compatible recipients, i.e., stem cells from donors with rare HLA types could be maintained in banks for eventual use by multiple recipients. The cells could be made available upon demand, thus avoiding delay. These cells could be extremely well characterized so that their functional properties are defined and consistent from recipient to recipient. This would be particularly important for patients with rare HLA types and for minorities. The expanded cells could also include more mature progenitor cells which may facilitate more rapid engraftment.

This invention can be further applied to allow expansion of engineered cells in vivo. Current procedures for gene therapy using hemopoietic stem cells, for example, require ablation of the patients' bone marrow via irradiation and/or in vivo selection using a cytotoxic drug. The subject invention provides an improved method for conducting hemopoietic stem cell therapy. The method offers a radically improved prognosis for stem cell gene therapy and avoids the need for myeloablative conditioning. Specifically, one first harvests stem cells from a mammalian donor, typically from bone marrow or from peripheral blood, generally after stem cell mobilization, as described in Example 7. The harvested cells are then transduced with DNA constructs encoding one or more dimerizer dependent signaling proteins as described elsewhere herein, and then introduced (or reintroduced) into the recipient. Dimerizer is then administered to the recipient to trigger expansion of the introduced genetically engineered cells. Since the engineered cells exhibit a dimerizer-dependent growth advantage over non-engineered cells, over a period of time the bone marrow should repopulate with healthy, engineered cells. Because stem cells and progenitors may be a small percentage of the harvested cells, the collected material may be subjected to procedures to enrich for stem cells and progenitors before being transduced with the recombinant DNA. Also, after transduction, the cells may be exposed to dimerizer in one or more preliminary rounds of expansion, if desired.

By eliminating the need for myeloablative treatment, it is now possible to envision a pattern of treatment analogous to kidney dialysis in which the patient undergoes periodic cycles of repeated therapy. In this case, the patient is subjected to mobilization (at least in certain embodiments of the invention), harvest, transduction, introduction of engineered cells and treatment with dimerizer, and the cycle is repeated one or more times as needed. Once a month, for example, for a period of months or longer, stem and progenitor cells may be harvested, transduced and reintroduced into the patient. Dimerizer is administered to the patient, preferably orally, in an amount and for a duration sufficient to induce expansion of the desired hemopoietic cells. Again, since the engineered cells grow at a faster rate than non-engineered cells, engineered cells will eventually populate the bone marrow.

These methods also are beneficial for solid organ transplantation, since recent evidence suggests that successful transplantation is facilitated by engraftment of a small number of donor stem cells. For example, it has been shown that intrathymic injection of bone marrow cells into non-human primates enabled skin grafts to last twice as long as in control animals (Allen, et al. *Cell Immunol,* 181:127, 1997). In addition, irradiated mice which received liver transplants were able to repopulate their bone marrow with donor-derived stem cells that migrated from the transplanted liver to the bone marrow (see Starzl, et al. *Nature Medicine* 2:163, 199 and accompanying references). Thus, if a population of stem cells were transfected ex vivo and introduced into a transplant patient, these cells could then be induced to expand and facilitate engraftment of the transplant.

Methods of this invention can also be used for treatment of genetic disorders such as thalassemias, in which the cells contain a defective globin gene. It is known in the art that thalassemias can be cured by ablation of a patient's bone marrow and administration of donor cells which contain a wild-type copy of the globin gene. With a system for regulatable proliferation, one may now administer the donor cells without ablating the patient's own cells. Dimerizer may then be administered to the patient in an amount and for a duration permitting the faster-growing donor cells to populate the bone marrow and produce the wild-type protein (as can be observed indirectly by amelioration of the severity or frequency of symptoms). In an alternative embodiment, the patient's own bone marrow may be harvested, transduced with the wild-type globin gene along with the DNA encoding the fusion proteins, and then reintroduced.

Many other therapeutic applications can be envisioned in which at least one additional construct is transduced into the cells along with the DNA encoding the fusion proteins. For example, hepatocytes which express antisense hepatitis C mRNA could be given to patients with hepatitis C, or one could expand T lymphocytes which express a product that confers resistance to HIV. In these embodiments, the therapeutic gene may be expressed constitutively or regulatably.

In another embodiment, cells can be grown using the methods of this invention to achieve a population of a specific differentiated cell type, e.g., megakaryocytes. The cells would be expanded until megakaryocytes are the predominant cell type, and could then be administered to a patient for treatment of thrombocytopenia. Alternatively, erythroid progenitor cells can be expanded and given to patients with anemia.

Stem and precursor cells can also be harvested from the central nervous system, e.g., from fetal tissue, and provide important tools for treatment of diseases and disorders such as Parkinson's disease, spinal cord injury, multiple sclerosis and other neurodegenerative disorders. (See e.g., Mayer-Pröschel, et al. *Journal of NIH Research* 9:31, 1997; Fisher, *Neurobiol Dis.,* 4:1, 1997; and references cited in both papers). For example, neuron-restricted precursor cells and glial-restricted precursor cells may be recovered, transduced with DNA constructs encoding one or more fusion proteins of this invention to permit dimerizer-dependent growth/proliferation and/or differentiation, and then introduced into a human or non-human mammal, e.g., by intracerebral transplantation. Administration of dimerizer to the recipient mammal initiates dimerizer-dependent signaling, thus constituting a method for providing replacement therapy and/or repairing damaged tissue. In the design of fusion proteins for such CNS applications, signaling domains from receptors for factors such as neurotrophin-3, bFGF, thyroid hormone T3 and ciliary neurotrophic factor are of special interest, as are signaling domains derived from downstream components of signaling pathways descending from such receptors. If desired, the cells may be subjected to one or more rounds of dimerizer-dependent expansion ex vivo, prior to introduction of engineered cells into the recipient. The precursors may also be transduced with one or more accessory DNA constructs encoding therapeutic factors that promote neuron survival and/or regeneration or that have other desired pharmacologic activities. (See, e.g., Mayer-Pröschel, et al. 1997, and Fisher, et al. 1997.)

A wide variety of diseases and pathological conditions may thus be treated by ex vivo and/or in vivo expansion of an appropriate population of genetically engineered cells in accordance with this invention. Illustrative examples are provided in the following Table 2.

TABLE 2

| Disease/Condition | Cell Type to be Expanded |
| --- | --- |
| cirrhosis, hemophilia, hereditary tyrosinemia, Wilson's disease, hepatitis | Liver cells |
| Grafts for burn patients | Keratinocytes and fibroblasts |
| peripheral nerve injury, spinal cord injury, brain injury, Parkinson's disease (basal ganglia cells), multiple sclerosis, Guilliaume Barre syndrome | Nerve cells |
| muscular dystrophy | Skeletal muscle |
| Hirschsprung's disease | Smooth muscle |
| cardiomyopathy | Cardiac muscle |
| fractures | Osteoblasts |
| osteopetrosis | Osteoclasts |
| mucositis following chemotherapy, crohn's disease, ulcerative colitis | Intestinal cells |
| cystic fibrosis | Lung |
| diabetes mellitus, chronic pancreatitis | Pancreas |
| Addison's disease | Adrenal cortex |
| avascular necrosis (occurs in patients treated with steroids and in patients with sickle cell anemia), coronary artery disease, cerebrovascular disease (improve blood flow to the brain) | Vascular endothelial cells |
| diabetes insipidus | Pituitary |
| Parkinson's | Basal ganglia |
| All of the above | Human embryonic stem cells |

Pharmaceutical Compositions and Their Administration to Subjects Containing Engineered Cells Administration The drug may be administered as desired using pharmaceutically acceptable materials and methods of administration. Depending upon factors such as the binding affinity of the drug, the response desired, the manner/route of administration, the biological half-life and bioavailability of the drug, the number of engineered cells present, etc., various protocols may be employed. The drug may be administered parenterally, or more preferably orally. Dosage and frequency of administration will depend upon factors such as described above. The drug may be taken orally as a pill, powder, or dispersion; bucally; sublingually; injected intravascularly, intraperitoneally, subcutaneously; or the like. The drug (and antagonists, as discussed below) may be formulated using conventional methods and materials well-known in the art for the various routes of administration. The precise dose and particular method of administration will depend upon the above factors and be determined by the attending physician or health care provider.

The particular dosage of the drug for any application may be determined in accordance with conventional approaches and procedures for therapeutic dosage monitoring. A dose of the drug within a predetermined range is given and the patient's response is monitored so that the level of therapeutic response and the relationship of target gene expression level over time may be determined. Depending on the expression levels observed during the time period and the therapeutic response, one may adjust the level of subsequent dosing to alter the resultant expression level over time or to otherwise improve the therapeutic response. This process may be iteratively repeated until the dosage is optimized for therapeutic response. Where the drug is to be administered chronically, once a maintenance dosage of the drug has been determined, one may conduct periodic follow-up monitoring to assure that the overall therapeutic response continues to be achieved.

In the event that the activation by the drug is to be reversed, administration of drug may be suspended so that cells return to a basal rate of proliferation. To effect a more active reversal of therapy, an antagonist of the drug may be administered. An antagonist is a compound which binds to the drug or drug-binding domain to inhibit interaction of the drug with the fusion protein(s) and thus inhibit the downstream biological event. Antagonists include drug analogs, homologs or components which are monovalent with respect to the fusion proteins. Such compounds bind to the fusion proteins but do not support clustering of the fusion proteins as is required for activation of signaling. Thus, in the case of an adverse reaction or the desire to terminate the therapeutic effect, an antagonist can be administered in any convenient way, particularly intravascularly or by inhalation/nebulization, if a rapid reversal is desired.

Compositions

Drugs for use in this invention can exist in free form or, where appropriate, in salt form. The preparation of a wide variety of pharmaceutically acceptable salts is well-known to those of skill in the art. Pharmaceutically acceptable salts of various compounds include the conventional non-toxic salts or the quaternary ammonium salts of such compounds which are formed, for example, from inorganic or organic acids of bases.

The drugs may form hydrates or solvates. It is known to those of skill in the art that charged compounds form hydrated species when lyophilized with water, or form solvated species when concentrated in a solution with an appropriate organic solvent.

The drugs can also be administered as pharmaceutical compositions comprising a therapeutically (or prophylactically) effective amount of the drug, and a pharmaceutically acceptable carrier or excipient. Carriers include e.g., saline, buffered saline, dextrose, water, glycerol, ethanol, and combinations thereof, and are discussed in greater detail below. The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Formulation may involve mixing, granulating and compressing or dissolving the ingredients as appropriate to the desired preparation.

The pharmaceutical carrier employed may be, for example, either a solid or liquid.

Illustrative solid carriers include lactose, terra alba, sucrose, talc, gelatin, agar, pectin, acacia, magnesium stearate, stearic acid and the like. A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Illustrative liquid carriers include syrup, peanut oil, olive oil, water, etc. Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g., cellulose derivatives, preferably sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can also be an oily ester such as ethyl oleate and isopropyl myristate. Sterile liquid carders are useful in sterile liquid form compositions for parenteral administration. The liquid carrier for pressurized compositions can be halogenated hydrocarbon or other pharmaceutically acceptable propellant. Liquid pharmaceutical compositions which are sterile solutions or suspensions can be utilized by, for example, intramuscular, intraperitoneal or subcutaneous injection. Sterile solutions can also be administered intravenously. The drugs can also be administered orally either in liquid or solid composition form.

The carrier or excipient may include time delay material well-known to the art, such as glyceryl monostearate or glyceryl distearate along or with a wax, ethylcellulose, hydroxypropylmethylcellulose, methylmethacrylate and the like. When formulated for oral administration, 0.01% Tween 80 in PHOSAL PG-50 (phospholipid concentrate with 1,2-propylene glycol, A. Nattermann & Cie. GmbH) may be used as an oral formulation for a variety of drugs for use in the practice of this invention.

A wide variety of pharmaceutical forms can be employed. If a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable solution or suspension in an ampule or vial or nonaqueous liquid suspension.

To obtain a stable water soluble dosage form, a pharmaceutically acceptable salt of the drug may be dissolved in an aqueous solution of an organic or inorganic acid, such as a 0.3M solution of succinic acid or citric acid. Alternatively, acidic derivatives can be dissolved in suitable basic solutions. If a soluble salt form is not available, the compound is dissolved in a suitable cosolvent or combinations thereof. Examples of such suitable dissolved in a suitable cosolvent or combinations thereof. Examples of such suitable cosolvents include, but are not limited to, alcohol, propylene glycol, polyethylene glycol 300, polysorbate 80, glycerin, polyoxyethylated fatty acids, fatty alcohols or glycerin hydroxy fatty acids esters and the like in concentrations ranging from 0-60% of the total volume.

Various delivery systems are known and can be used to administer the drugs, or the various formulations thereof, including tablets, capsules, injectable solutions, encapsulation in liposomes, microparticles, microcapsules, etc. Preferred routes of administration to a patient are oral, sublingual and bucal. Methods of introduction also could include but are not limited to dermal, intradermal, intramuscular, intraperitoneal, intravenous, subcutaneous, intranasal, pulmonary, epidural, ocular and (as is usually preferred) oral routes. The drug may be administered by any convenient or otherwise appropriate route, for example by infusion or bolus injection, by absorption through epithelial or mucocutaneous linings (e.g., oral mucosa, rectal and intestinal mucosa, etc.) and may be administered together with other biologically active agents. Administration can be systemic or local. For ex vivo applications, the drug will be delivered as a liquid solution to the cellular composition.

In a specific embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the side of the injection. Generally, the ingredients are supplied either separately or mixed together in unit dosage form, for example, as a lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In addition, in certain instances, it is expected that the compound may be disposed within devices placed upon, in, or under the skin. Such devices include patches, implants, and injections which release the compound into the skin, by either passive or active release mechanisms.

Materials and methods for producing the various formulations are well-known in the art and may be adapted for practicing the subject invention. See, e.g., U.S. Pat. Nos. 5,182,293 and 4,837,311 (tablets, capsules and other oral formulations as well as intravenous formulations) and European Patent Application Publication Nos. 0 649 659 (published Apr. 26, 1995; rapamycin formulation for IV administration) and 0 648 494 (published Apr. 19, 1995; rapamycin formulation for oral administration).

The effective dose of the drug will typically be in the range of about 0.01 to about 50 mg/kgs, preferably about 0.1 to about 10 mg/kg of mammalian body weight, administered in single or multiple doses. Generally, the compound may be administered to patients in need of such treatment in a daily dose range of about 1 to about 2000 mg per patient. In embodiments in which the compound is rapamycin or an analog thereof with some residual immunosuppressive effects, it is preferred that the dose administered be below that associated with undue immunosuppressive effects.

The amount of a given drug which will be effective in the treatment or prevention of a particular disorder or condition will depend in part on the severity of the disorder or condition, and can be determined by standard clinical techniques. In addition, in vitro or in vivo assays may optionally be employed to help identify optimal dosage ranges. Effective doses may be extrapolated from dose-response curves derived from in vitro or animal model test systems. The precise dosage level should be determined by the attending physician or other health care provider and will depend upon well-known factors, including route of administration, and the age, body weight, sex and general health of the individual; the nature, severity and clinical stage of the disease; the use (or not) of concomitant therapies; and the nature and extent of genetic engineering of cells in the patient.

The drugs can also be provided in a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceutical or biological products, which notice reflects approval by the agency of manufacture, use or sale for human administration.

EXAMPLES

Example 1

Illustrative Dimerizing Agents

FK1012 consists of two molecules of the natural product FK506 covalently joined to one another by a synthetic linker and can be prepared from FK506 using published procedures. See, e.g., PCT/US94/01617 and Spencer, et al. *Science* 262: 1019, 1993. FK1012 is capable of binding to two FKBP domains and functioning as a cross-linking-type dimerizing agent for FKBP-containing chimeric proteins.

AP1510 (Amara, et al. *Proc. Natl. Acad. Sci. USA* 94:10618, 1997), AP1903 (Clackson, et al. *Proc. Nail. Acad. Sci. USA* 95:10437, 1998) and AP20187 are other synthetic dimerizer molecules that can be used to induce dimerization of FKBP12- or FKBP12(F36V)-containing fusion proteins. In experiments to date, AP1510 and AP20187 have shown no immunosuppressive activity or other toxicity to cells.

molecule, in which two copies of a synthetic FKBP ligand are covalently linked through a shared linker moiety.

AP1510 generally outperforms FK1012 protein dimerization applications. AP1510 has been successfully used to dimerize a number of transmembrane receptors that are activated by oligomerization.

As AP1510 is a completely synthetic molecule, it readily supports modification and optimization for a given application. A variety of other synthetic dimerizing agents are disclosed in WO 96/06097 and WO 97/31898 for binding to FKBP-related domains, such as:

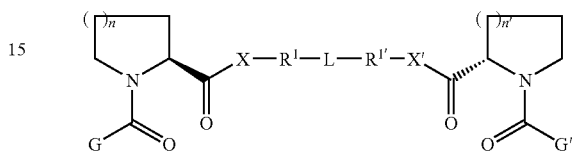

wherein X and X' can be O, NH, or $CH_2$;

L is a covalently linker moiety;

wherein G and G' are independently selected from the group comprised of

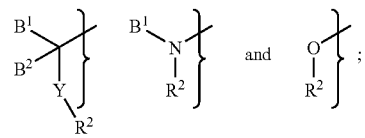

$B^1$ and $B^2$ are each independently hydrogen, alkyl, alkenyl, alkynyl, cycloalkyl, cycloalkenyl, cycloalkynl, heteroalkyl,

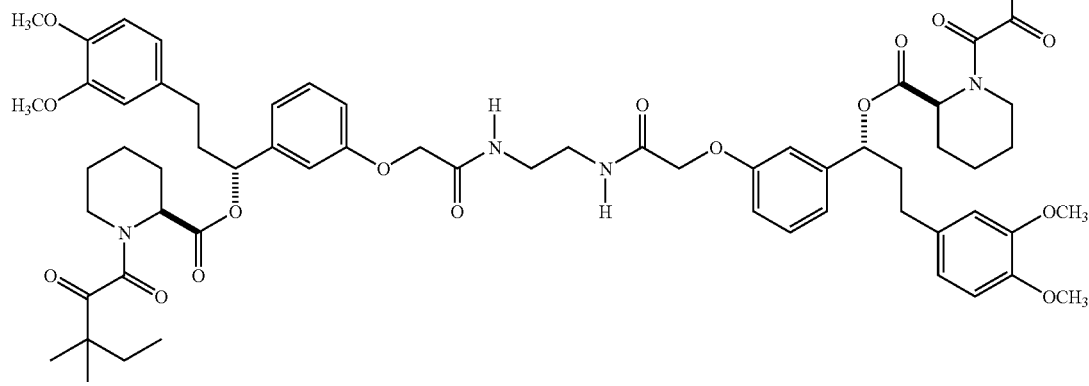

AP1510 is conceptually related to FK1012, the prototype homodimerizer. Both molecules are symmetrical homodimers of FKBP12 ligands. FK1012 is a semi-synthetic dimer of the natural product FK506. Positioning of the linker in the calcineurin binding domain of FK506 abolishes immunosuppressive activity while leaving FKBP12 binding unaffected. AP1510 is a smaller, simpler and completely synthetic heteroalkenyl, heteroalkynyl, heterocycloalkyl, heterocycloalkenyl, heterocycloalkynyl, aryl, substituted aryl, or heteroaryl moieties;

Y is O, S, NH, —NH(C═O)—, NH(C═O)—O—, $NH(SO_2)$—, $NR^3$, or a covalent bond;

$R^1$, $R^{1'}$, and $R^2$ are the same or different and are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkayl, substituted aryl, aryl, or heteroaryl moieties;

n and n' are each independently 1 or 2;

wherein at least one of X—$R^1$ and X'—$R^{1'}$ is independently a moiety:

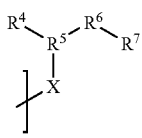

wherein $R^4$ is hydrogen; branched, unbranched, cyclic, saturated or unsaturated, substituted or unsubstituted aliphatic; branched, unbranched or cyclic heteroaliphatic; aryl or heteroaryl;

$R^5$ is a branched, unbranched or cyclic, aliphatic moiety of 1 to 8 carbon atoms;

$R^6$ is a substituted or unsubstituted aliphatic, heteroaliphatic, heterocyclic, aryl or heteroaryl moeity; and $R^7$ is hydrogen or a reactive functional group permitting covalent attachment to a linker moiety.

Two factors limit the use of FK1012 and AP1510 for in vivo studies. First, FK1012 and AP1510 are available only in limited quantities: they cannot be purchased, and must be chemically synthesized. Second, the in vivo half life of FK1012 is less than one hour, severely impeding efforts to extend in vitro observations to the in vivo setting. Because of these limitations, the in vivo studies have been performed with an alternative synthetic dimerizer, called AP20187.

Reconstituting AP1510

AP1510 (molecular weight 1190 Da) may be stored in lyophilized form. It should be reconstituted as a concentrated stock in an organic solvent. It is recommended that the lyophilized material be dissolved in absolute ethanol to make a 1 mM solution (e.g., dissolve 250 mg AP1510 in 210 ml ethanol). After adding the appropriate volume of ice-cold ethanol, seal and vortex periodically over a period of a few minutes to dissolve the compound. Keep on ice during dissolution to minimize evaporation.

Storing and Handling AP1510

Once dissolved, the stock solution can be kept at −20° C. indefinitely, in a glass vial or an eppendorf tube. Further dilutions in ethanol can be similarly stored. At the bench, solutions in ethanol should always be kept on ice, and opened for as short a time as possible, to prevent evaporation and consequent changes in concentration.

Using AP1510

Working concentrations of AP1510 can be obtained by adding compound directly from ethanol stocks, or by diluting serially in culture medium just before use. In the latter case it is recommended that the highest concentration not exceed 5 uM, to ensure complete solubility in the (aqueous) medium. In either case, the final concentration of ethanol in the medium added to mammalian cells should be kept below 0.5% (a 200-fold dilution of a 100% ethanol solution) to prevent detrimental effects of the solvent on the cells.

Example 2

Protocol for Preparing Constructs Encoding Dimerizable Fusion Proteins

Constructs encoding a desired fusion protein comprising one or more signaling domains and one or more FKBP domains may be conveniently assembled using the vectors pCF1E and pCMF2E, which may be obtained from ARIAD Pharmaceuticals Inc., 26 Landsdowne Street, Cambridge, Mass. 02139 (www.ariad.com). Those vectors provide an assortment of components that can be easily manipulated to generate protein fusions whose activity and localization can be controlled by dimerizer.

pCF1E

Inserts cloned into pCF1E as XbaI-SpeI fragments are transcribed under control of the human CMV enhancer promoter (C) and are expressed with a carboxy-terminal epitope tag (E, a 9 amino acid portion of the influenza hemagglutinin [HA] gene). The XbaI-SpeI insert in pCF1E contains a single copy of FKBP12 (F1). The amino terminus of this fusion protein (upstream of the XbaI site) consists only of a methionine and an alanine. Thus, the localization of the fusion protein is determined by that which is fused to FKBP12, since FKBP12 alone will be localized predominantly to the cytoplasm.

pCMF2E

Inserts cloned into pCMF2E as XbaI-SpeI fragments are transcribed under control of the human CMV enhancer promoter (C) and are expressed with an amino-terminal myristoylation-targeting peptide (M) from the amino terminus of v-src and a carboxy-terminal epitope tag (E, a 9 amino acid portion of the influenza hemagglutinin [HA] gene). The myristoylation sequence directs the fusion protein to cellular membranes. The XbaI-SpeI insert in pCMF2E contains two tandem copies of FKBP12 (F2).

Cloning Strategy

The basic strategy for creating protein fusions as in this example is to amplify the coding sequence of interest so that it contains the six nucleotides specifying an XbaI site immediately 5' to the first codon (taking appropriate care to avoid creating an overlapping Dam methylation sequence) and the six nucleotides specifying a SpeI site immediately 3' to the last codon. Then, for example, to create a construct encoding a fusion protein in which the insert is amino terminal to 2 FKBPs, clone the XbaI-SpeI fragment into the XbaI site of pCMF2E (XbaI and SpeI have compatible cohesive ends). If inserted in the proper orientation, the XbaI and SpeI sites, now flanking the new fusion protein, will be maintained, with the junction of the two peptides consisting of the two amino acids specified by the SpeI and XbaI sites that were fused. Or to fuse the XbaI-SpeI fragment carboxy-terminal to 2 FKBPs, insert it into the SpeI site of pCMF2E. In both cases, since the flanking XbaI and SpeI sites are maintained, additional fragments can still be fused at the amino- and carboxy-terminal ends.

This strategy can also be applied to create three tandem FKBPs. For example, the XbaI-SpeI fragment of pCMF1E can be inserted into the SpeI site of pCMF2E (or vice versa).

If the sequence to be fused contains internal XbaI or SpeI sites, fusions can still be made either by using XbaI or SpeI at both ends, or by using NheI or AvrII which also generate ends that are compatible with XbaI and Spa Note, though, that in these cases the flanking XbaI and SpeI sites will not be regenerated.

The sequence between the SpeI and BamHI sites of both vectors encodes a carboxy-terminal HA epitope tag followed by a stop codon. Therefore, stop codons should not be included in the fused sequences.

Finally, XbaI-SpeI or XbaI-BamHI fragments can be cloned into either the pCM- or pC-vector backbones to create fusion proteins containing or lacking amino-terminal myristoylation-targeting peptide sequence, respectively.

Example 3

Constructs for Fusion Proteins Containing c-kit, Epo-R & mpl Cytoplasmic Domains c-kit F3, also designated pMF(PK)3E (Belshaw, et al. *Proc. Nail. Acad Sci USA* 93:4604, 1996), is a modified form of pMF3E (Spencer, et al. *Science* 262:1019, 1993). FKBP12 has been modified to contain the mutations G89P and I90K. These mutations abrogate the ability of the FK506 complexes of this mutant FKBP to interact with calcineurin (Liu, et al. *Cell* 66:807, 1991) and have a reduced propensity to interact with cellular proteins (Belshaw, et al. 1996). A 1296 or 1164 base pair cytoplasmic domain of the murine c-kit was amplified by PCR using Pfu polymerase, a plasmid containing the c-kit cDNA as a template and one of the following primer pairs: 5' CCC CTC GAG TAC AAA TAT TTG CAG AAA CC 3' (upstream primer) [SEQ ID NO: 6] and 5' CCC CTC GAG GGC ATC TTC GTG CAC 3' (downstream primer [SEQ ID NO: 7]; amplified fragment encodes 432 amino acids) or 5' CCC CTC GAG CTT GGT GCT GTC CGA GAT 3' (downstream primer [SEQ ID NO: 8]; amplified fragment encodes 388 amino acids). The PCR amplified fragments were digested using Xho I, gel purified, and inserted into a Xho I digested and phosphatased pBluescript vector. Following sequence confirmation using the PRISM system (Applied Biosystems), the fragment was released from pBluescript by Xho I digestion and was ligated into the phosphatased Sal I digested plasmids F3 or F1 to generate the plasmids F3c-kit432, F3c-kit388 and F1c-kit432. Plasmids were purified over two sequential cesium chloride gradients prior to transfection.

Epo

F3, also designated pMF(PK)$_3$E (Beishaw, et al. *Proc. Natl. Acad. Sci. USA* 93:4604, 1996) is a modified form of pMF3E (Spencer, et al. *Science* 262:1019, 1993). FKBP12 has been modified to contain the mutations G89P and I90K. These mutations abrogate the ability of the FK506 complexes of this mutant FKBP to interact with calcineurin (Liu, et al. *Cell* 66:807, 1991) and have a reduced propensity to interact with cellular proteins (Belshaw, et al. *Proc. Natl. Acad. Sci. USA* 93:4604, 1996). 708 or 309 basepair fragments of the murine EpoR (D'Andrea, et al. *Cell* 57:277, 1989) were amplified by PCR using the plasmid pXM(EpoR)-190 (a kind gift of J. Prchal) as a template and one of the following primer pairs: 5' CCC CTC GAG TCC CAC CGC CGG ACT CTG 3' (upstream primer [SEQ ID NO: 9]) and 5' CCC CTC GAG GGA GCA GGC CAC ATA GC 3' (downstream primer [SEQ ID NO: 10]; resulting fragment has 708 bp) or 5' CCC CTC GAG CAA CCA CTT ATC CAA TAC 3' (downstream primer [SEQ ID NO: 11]; resulting fragment has 309 bp). The PCR amplified fragments were digested using XhoI, gel purified, and ligated into the phosphatased SaII digested plasmids F3 or F1 to generate the plasmids F3EpoR236, F3EpoR103 and F1EpoR236, and sequenced using the PRISM system (Applied Biosystems). Plasmids were purified using two rounds of cesium chloride centrifugation prior to transfection.

Mpl

The mpl cytoplasmic domain was amplified by PCR using Pfu polymerase, a plasmid containing the murine mpl cDNA as a template and the following primer pair: 5' GG CTC GAG AAG TGG CAA TTT CCT GCG 3' [SEQ ID NO: 4], and 5' GG CTC GAG GGG CTG CTG CCA ATA GC 3' [SEQ ID NO: 5]. The PCR amplified fragment was digested using XhoI, gel purified and inserted into an XhoI digested and phosphatased pBluescript vector. Following sequence confirmation using the PRISM system (Applied Biosystems), the fragment was released from pBluescript by XhoI digestion and was ligated into the phosphatased SaII digested plasmids F3 or F1 to generate the plasmids F3mpl or F1mpl. Plasmids were purified over two sequential cesium chloride gradients prior to transfection. Construction of MSCVF1mpl: The F1mpl fragment was released from its parent vector by KspI digestion blunt ending with T4 DNA polymerase followed by digestion with BglII. This fragment was inserted into an XhoI digested, blunted, then BglII digested MSCVneoEB (Hawley, et al. *Gene Ther.* 1:136, 1994).

Example 4

Isolation of Bone Marrow and Co-Culturing of Bone Marrow Cells

Forty-eight hours following administration of 150 mg/kg 5-fluorouracil (5-FU), marrow cells were harvested from B6D2F1 mice and cultured for 48 hours in Dulbecco's Modified Eagle's Medium containing 16% fetal calf serum (Intergen), 5% IL3-conditioned medium (Stem Cell Technologies), 100 ng/ml recombinant human IL6 and 50 ng/ml recombinant murine stem cell factor in a 37° C., 5% $CO_2$ incubator. After 48 hours, cells were transferred onto irradiated (1500 cGy) producer cells and cocultivated using the same growth conditions except for the addition of polybrene (8 mg/ml). Marrow cells were harvested after 48-hours of cocultivation.

Example 5

Generation of Retroviral Producer Lines for Infection of Bone Marrow

Retrovirus producer lines for MSCVNeo, MSCVF1BP, MSCVF1Mpl and MSCVF36VMpl were generated by first transfecting the amphotropic packaging line PA17 (Miler, et al. *Mol. Cell. Biol.* 2895, 1986) with vector plasmid, and two days later collecting supernatant and transducing the ecotropic packaging line GpE+86 (Markowitz, et al. *J. Virol.* 62:1120, 1988). Producer clones were then isolated under G418 selection and screened for virus titer based on end-point titration using NIH3T3 cells (Bodine, et al. *Proc. Natl. Acad. Sci. USA* 87:3738, 1990). Producer clones were isolated for each vector with titers between $10^5$ and $10^6$ colony-forming units per ml. Genetic stability was confirmed by Southern analysis of clones and pools of producer cells using the restriction enzyme KpnI, which cuts once in each LTR, and probing for the neo gene. Producer lines were free of helper-competent virus using a marker-rescue assay as previously described (Miller and Rosmann, *BioTechniques* 7:980, 1989). All cell lines were cultured at 37° C. in Dulbecco's modified Eagle's medium (DMEM; Gibco/BRL Life Technologies, Grand Island, N.Y.) supplemented with 8% characterized fetal bovine serum (FBS; Gibco/BRL), sodium pyruvate and nonessential amino acids (Gibco/BRL), and 2 mM L-glutamine (Gibco/BRL).

Example 6

Dimerizer-Dependent Growth of Genetically Engineered Bone Marrow Cells

Figure 1B:
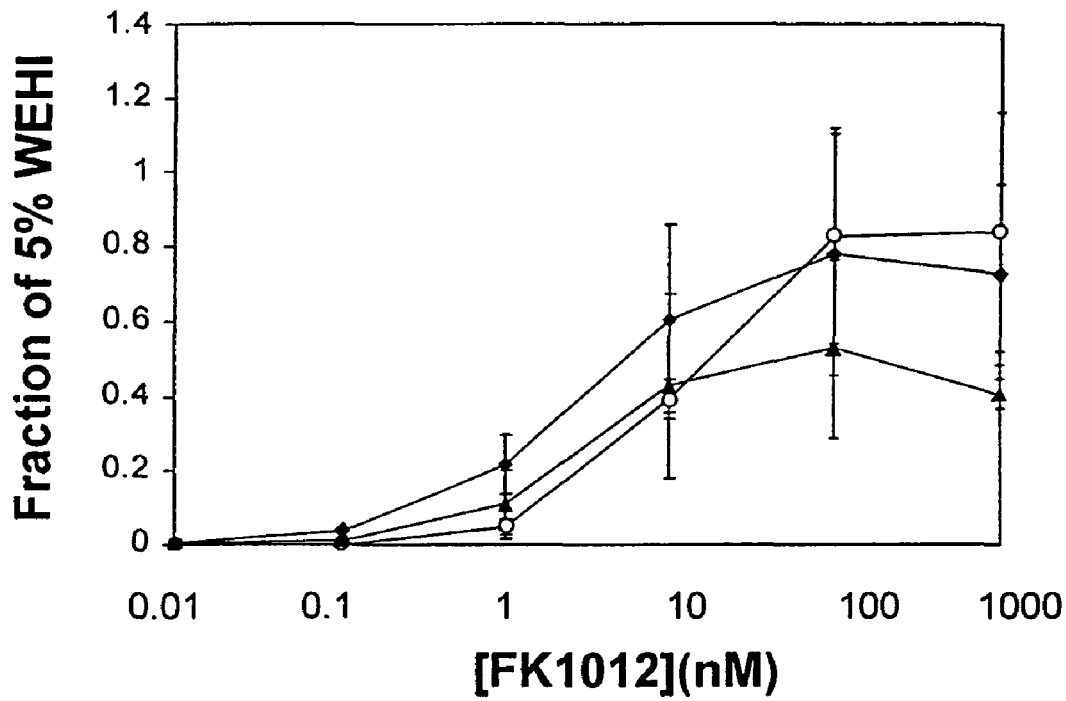
Figure 1C:
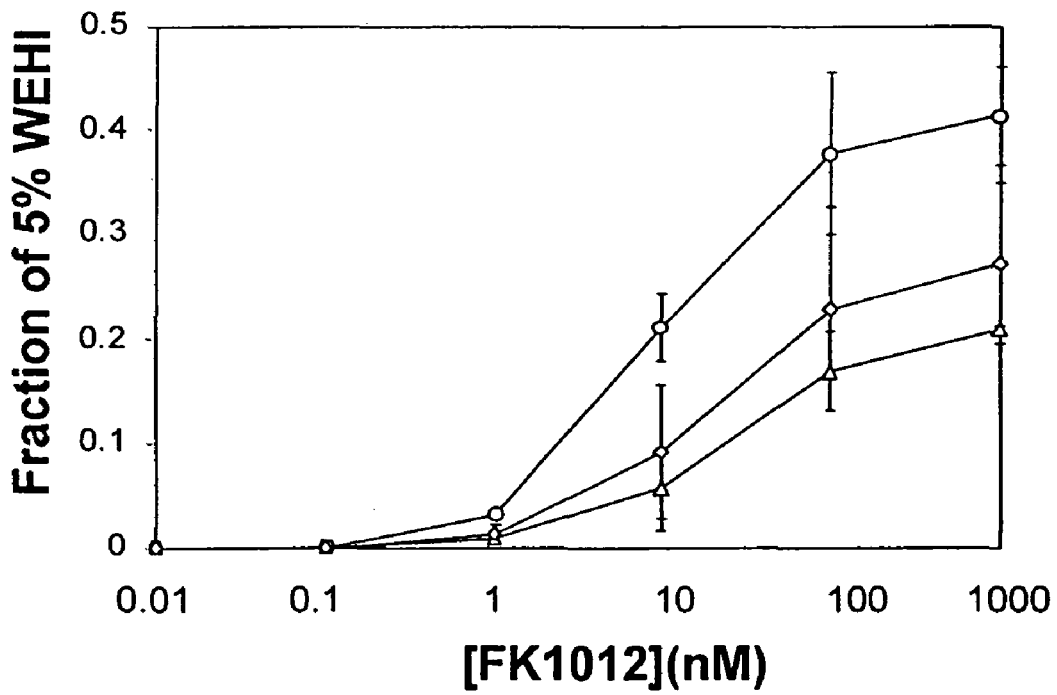
Figure 2:
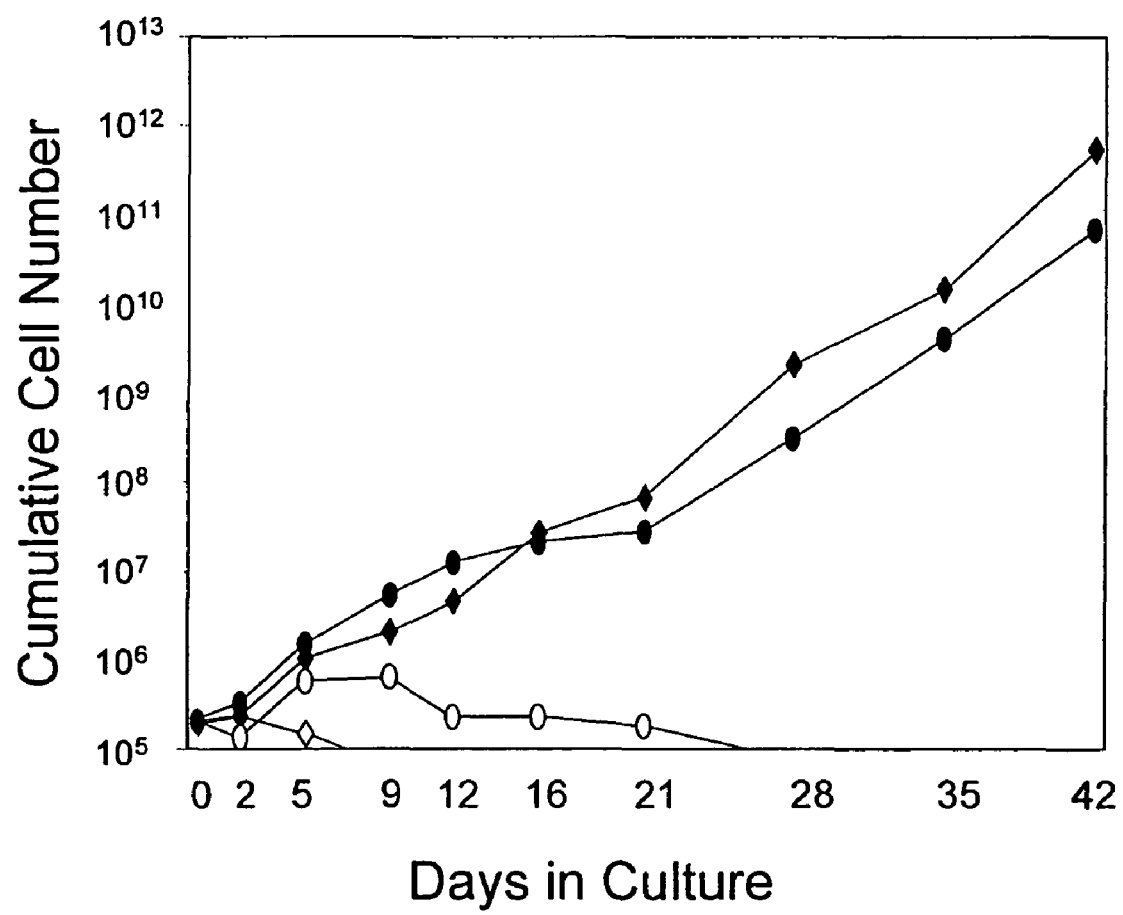
FIG. 2: FK1012 stimulates expansion of genetically modified bone marrow cells. Following retroviral transduction, marrow cells were cultured in IMDM containing 10% FCS, 50 U/ml penicillin, 50 mg/ml streptomycin either in the presence or absence of FK1012 (100 nM) or flt-3 ligand (Peprotech-100 ng/ml), in a 37°, 5% $CO_2$, incubator. Cell numbers were determined on the days indicated. Open diamonds: No FK1012, no FL; Closed diamonds: FK1012 alone; Open circles: FL alone; Closed circles: FK1012 plus FL. Note that X axis is on a logarithmic scale.

In order to test whether the pharmacological activation of mpl is capable of driving proliferation in genetically modified bone marrow cells, the F1mpl construct was inserted into the retroviral vector MSCV-neoEB (Hawley, et al. *Gene Ther.* 1:136, 1994). The resulting construct, MSCVF1mpl, was used to generate a stable, high titer, helper virus-free ecotropic producer cell line as described above. Supernatant from the producer cell line was capable of conferring G418 resistance and FK1012 responsiveness in transduced Ba/F3 cell clones (FIG. 1C). Gene transfer into murine bone marrow cells was performed by cocultivation, and transduced marrow cells were tested in suspension culture for the capacity to respond to FK1012. In one set of cultures, FK1012's effects were evaluated in the absence of added growth factors. In a second set of cultures, the effect of FK1012 was evaluated in the presence of flt-3 ligand (FL), since thrombopoietin and FL have previously been demonstrated to exert synergistic effects on hemopoietic cell expansion ex vivo (Piacibello, et al. *Blood* 89:2644, 1997). Cell numbers were determined at various time points of culture (FIG. 2). In the absence of drug or added growth factors, all cells died over a period of 7-14 days. FL alone produced a three-fold expansion in cell numbers between 9 and 12 days of suspension culture, however all cells died by day 28 of culture. In contrast, FK1012 dramatically stimulated cell proliferation. The proliferative effect of FK1012 was apparent within 5 days of culture, and has persisted for longer than 49 days without evidence of decline. The combination of FK1012 and FL exerted a more pronounced effect on cell growth than FK1012 alone during the first two weeks of culture, however FK1012 alone appeared to provide a similarly potent growth stimulus at later time points. By 42 days of culture FK1012 had induced a greater than 2.5 million-fold expansion in cell numbers.

The types of cells emerging in response to FK1012 differed at varying time points of culture. During the first two weeks of culture in FK1012, mature granulocytes and macrophages predominated, while megakaryocytes were rare. At later time points mature granulocytes were dramatically reduced and megakaryocytes emerged as the dominant phenotypically identifiable cell population. Morphologically similar findings were observed with the combination of FK1012 plus FL, with the exception that macrophages were more abundant than seen with FK1012 alone. Similar results were obtained in a second experiment.

In order to demonstrate that the proliferative effect of FK1012 is reversible, cells cultured for 28 days in the presence of FK1012 were tested for persistence of cell growth following FK1012 withdrawal. As shown in Table 3, withdrawal of FK1012 was followed promptly by cell death, while re-addition of FK1012 was associated with persistent cell growth.

TABLE 3

Reversibility of FK1012-dependent cell proliferation

| Growth Conditions | Day in Culture | | |
|---|---|---|---|
| | 0 | 7 | 14 |
| +FK1012 | 5 | 36 | 1283 |
| −FK1012 | 5 | 0.59 | .09 |

For the experiments whose results are shown in Table 3, after 28 days of culture in FK1012 (100 nM), transduced marrow cells were washed extensively and cultured in suspension in the presence (+) or absence (−) of FK1012. The numbers in Table 3 indicate the number of cells per well×$10^{-5}$.

Figure 3A:
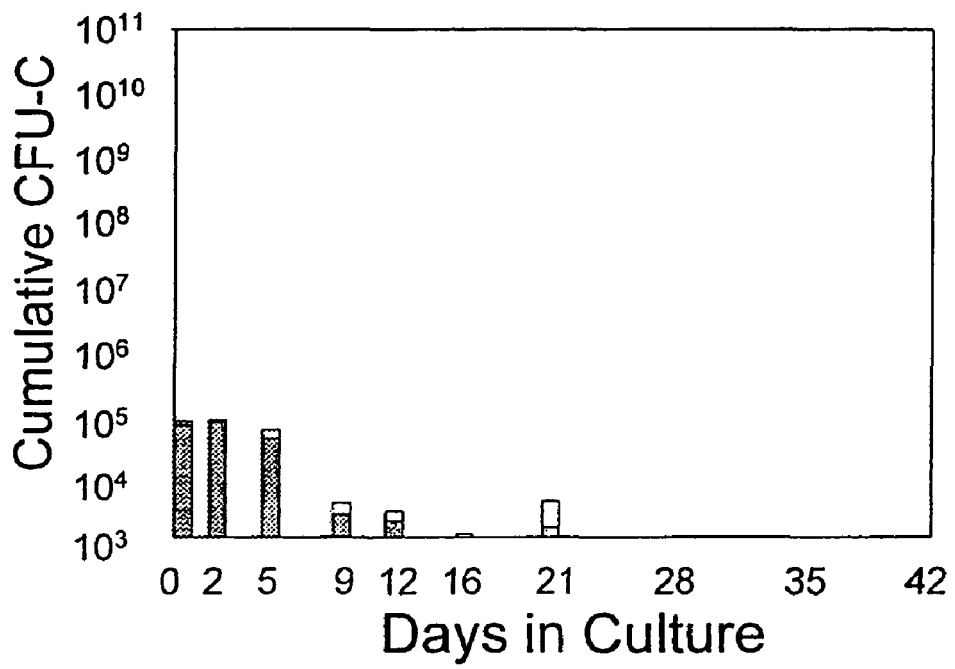
FIG. 3: CFU-C assays at various time points during suspension culture. Cells were harvested on the days indicated and cultured in semisolid media (Blau, et al. *Hum. Gen. Ther.* 7:2069, 1996) either in the presence or absence of G418. The concentration of G418, 800 mg/ml, was sufficient to prevent the growth of nontransduced cells (data not shown). Dark bars: CFU-C numbers in the absence of G418; Light bars: CFU-C numbers in the presence of G418. (A) No FK1012, no FL; (B) FK1012 alone; (C) FL alone; (D) FK1012 plus FL. Note that FK1012-mediated CFU-C expansion markedly favors the genetically modified cell population.
Figure 3B:
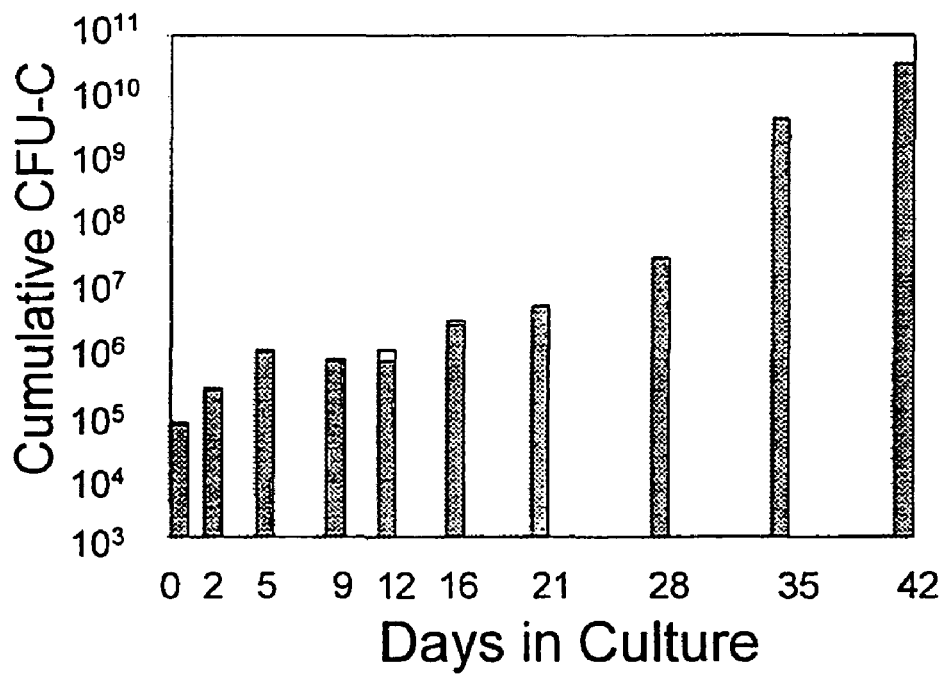
Figure 3C:
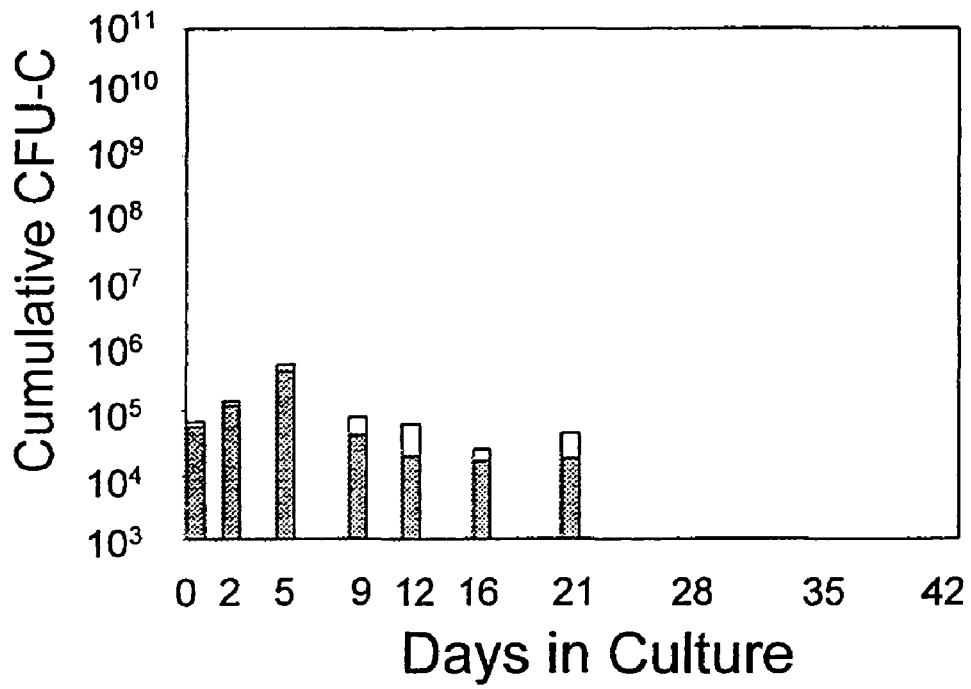
Figure 3D:
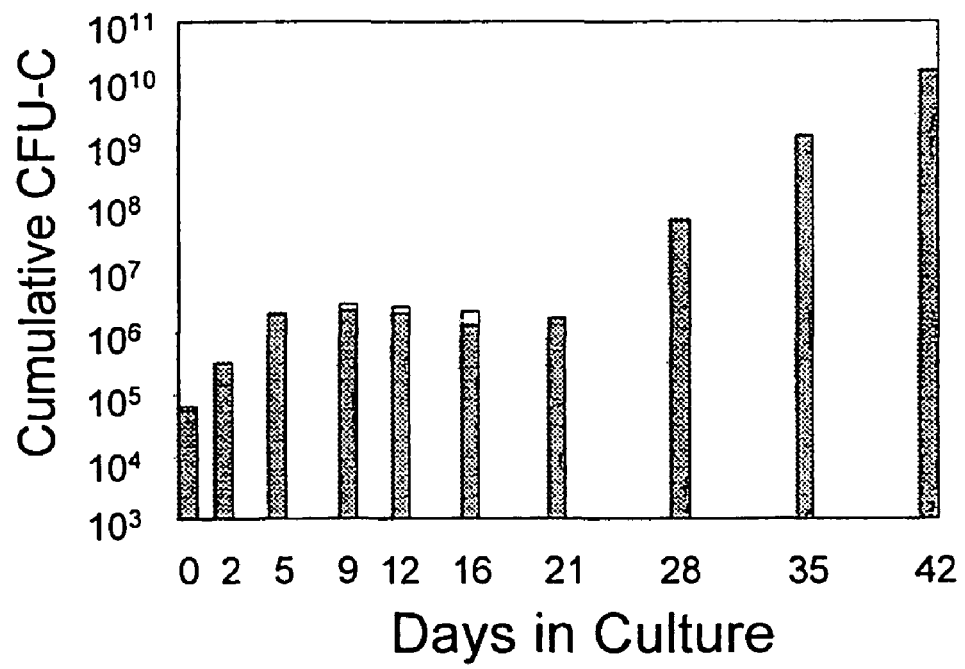

To determine whether FK1012 is capable of stimulating expansion among clonogenic progenitor cells, progenitors were assayed at various time points of culture as colony forming unit cells (CFU-C). As the MSCVF1mpl vector incorporates a neo gene. (Hawley, et al. *Gene Ther.* 1:136, 1994), the frequency of genetically modified progenitors is reflected in the frequency of G418 resistant CFU-C. In the absence of FK1012 CFU-C expansion failed to occur, and there was no preferential survival advantage in favor of G418 resistant CFU-C. By day 28 CFU-C had fallen to undetectable levels (FIG. 3A). In contrast, in the presence of FK1012 an almost 600,000-fold expansion in CFU-C was observed by day 42 (FIG. 3B). The vast majority of CFU-C were G418 resistant, suggesting a preferential proliferative advantage in favor of the genetically modified progenitor cell population. Of note is that while granulocytes were virtually absent after 42 days in suspension culture in the presence of FK1012 alone, CFU-C progeny derived from these cultures contained large numbers of granulocytes. Since CFU-C assays were performed in the presence of IL3, these findings suggest that myeloid progenitors arising in response to FK1012 require additional growth factors in order to accomplish terminal differentiation. Similar effects of FK1012 were observed in the presence of FL. FL alone produced a transient seven-fold expansion in CFU-C without preference for the transduced population (e.g., FIG. 3C). In contrast, the combination of FL and FK1012 produced a 260,000-fold expansion of transduced CFU-C by day 42 (FIG. 3D). A similar expansion of progenitors in response to FK1012 has been seen in a second experiment.

While the data presented above suggest that FK1012 selectively expands genetically modified progenitor cells, an assessment of preferential expansion is complicated by high baseline transduction rates into progenitors (consistently >80%). In order to determine whether FK1012 is capable of specifically delivering a mitogenic signal to a minor population of genetically modified CFU-C, marrow cells cocultivated with the MSCVF1mpl producer cell line were mixed with marrow cells cocultivated with the parental packaging cell line. The frequency of G418 CFU-C arising from this mixed population of transduced and non-transduced cells was 35%. As shown in Table 4, FK1012 selectively expanded the genetically modified progenitor cell population.

TABLE 4

FK1012-mediated selection of genetically modified CFU-C

| Day in Culture | No Drug | FK1012 | FL | FK1012 + FL |
|---|---|---|---|---|
| 0 | 0.35 | 0.35 | 0.35 | 0.35 |
| 7 | 0.24 | 0.96 | 0.14 | 0.98 |

The numbers in Table 4 indicate the fraction of G418 resistant CFU-C.

In addition to the potential utility of this system for therapeutic applications, the results obtained may provide insights into blood cell development. During the first two weeks of culture, FK1012 stimulated the expansion of multiple cell lineages, including granulocytes and macrophages. In contrast, at later time points of culture FK1012 directed the expansion of a cell population that was dominated by megakaryocytes with very few mature granulocytes. Despite the dramatic decline in mature granulocyte production, progenitors with the potential for granulocytic differentiation were retained, as evidenced by the emergence of granulocytes upon culture in the presence of IL3. FK1012's ability to stimulate terminal granulocytic maturation during the first two weeks of culture contrasts sharply with the loss of mature granulocytes at later time points. Among possible explanations for this phenomenon is that granulocytes arising in response to FK1012 at early time points in culture were derived from progenitors pre-programmed to a myeloid pathway of differentiation, and that signaling through mpl permitted their survival. In contrast, progenitors generated under the influence of FK1012 may require signals other than those provided by mpl in order to carry out granulocytic differentiation. The apparent inability of mpl to direct persistent granulocytic maturation is partially supported by recent studies using the full length mpl receptor. (Goncalves, et al. *Blood* 89:3544, 1997). Equally noteworthy is the dominance of megakaryocytes at later time points in the culture, suggesting that mpl activation preferentially promotes megakaryocytic differentiation. These findings provide preliminary support for an instructive model of hematopoietic cell development (Metcalf and Burgess, *J. Cell. Physiol.* 111:275, 1982; Lu, et al. *Blood* 87:525, 1996). A truncated mpl signaling domain may retain a preference for megakaryocytic differentiation, and deletion of putative differentiation domains may enable multilineage differentiation, as has been observed for the erythropoietin receptor (Kirby, et al. *Proc. Natl. Acad. Sci. USA* 93:9402, 1996).

Example 7

Construction of an MSCVneo-Based Retroviral Vector

A MSCVneo-based retroviral vector encoding a fusion protein identical to F1mpl except for the presence of the F36V mutation was built and tested. This vector, MFM (FIG. 4), has been used to derive a genetically stable, high titer ecotropic producer cell line using the methods described in Example 5. In the presence of AP20187, genetically modified primary murine bone marrow cells expressing the F36Vmpl fusion protein exhibit proliferative and differentiative responses that are indistinguishable from those we have observed using FK1012 (data not shown).

Example 8

In Vivo Selection Using the MFM Vector

Marrow cells from B6D2F1 mice were transduced as follows: fluorouracil, 150 mg/kg, was injected intraperitoneally into female B6D2F1 mice. Forty-eight hours later, marrow cells were harvested and cultured for 48 hours in DMEM containing 16% fetal calf serum, 5% IL-3 conditioned medium, 100 ng/ml recombinant IL-6, and 50 ng/ml recombinant murine stem cell factor in a 37° C., 5% $CO_2$ incubator. After 48 hours of prestimulation, cells were transferred onto irradiated (1500 cGy) producer cells and cocultivated using identical growth conditions except for the addition of polybrene (8 µg per ml). The producer cells generate retroviral particles containing the MFM vector that are able to infect the bone marrow cells. Therefore, the MFM retrovirus is introduced into the bone marrow cells during the period of cocultivation. Marrow cells were harvested after 48 hours of cocultivation and $8 \times 10^6$ cells were injected into each of 10 lethally irradiated (1050 cGy) B6D2F1 mice. Immediately following transplantation, five mice received intraperitoneal injections of AP20187 daily at a dose of 2 mg/kg/day for forty consecutive days. Five control mice received daily injections of the drug diluent (see below) without AP20187.

Dimerization Using AP20187

In contrast to FK1012, which binds FKBP12, AP20187 (Ariad Pharmaceuticals, Cambridge, Mass.) specifically binds an engineered version of FKBP12 in which a phenylalanine at amino acid position 36 has been replaced by a valine (F36V). AP20187 has two major advantages relative to FK1012: 1) AP20187 does not bind to endogenous FKBP12, and in many situations the drug is effective at lower concentrations than are required for FK1012; and 2) The in vivo half life of AP20187 is 9 hours, greatly improving the feasibility of in vivo studies.

Drug Formulation

AP20187 was prepared as follows: Drug was solubilized in ethanol, then PEG 400 was added. Finally, a mixture of water and Tween 80 was added to achieve final concentrations of ethanol of 4%, PEG400 10% and Tween 1.4%.

Effects of AP20187 on Hematopoietic Cells in the Femur

The presence of the neo gene in the MFM vector allows the frequency of genetically modified progenitor cells to be determined by performing clonogenic assays either in the presence or absence of G418. After 32 days of drug administration, bone marrow aspirates were performed and the frequency of clonogenic progenitor cells was determined. Results are shown as follows:

TABLE 5

Effects of AP20187 on G418 resistant colonies in the femur

|  | Percentage of G418 Resistant Colonies | Mean |
|---|---|---|
| Control Group | | |
| 188 | 19.6% | 10.42 (+/−12.3) |
| 190 | 1.8% | |
| 191 | 27.5% | |
| 192 | 2.6% | |
| 193 | 0.6% | |
| AP20187 Treated Group | | |
| 194 | 39.3% | 20.9 (+/−13.3) |
| 195 | 14.7% | |
| 196 | 17.7% | |
| 197 | 28.1% | |
| 198 | 4.6% | |

While the mean number of G418 resistant colony forming cells in the femur was approximately 2 fold higher in the AP20187-treated group, there was considerable variation between mice, and these differences did not achieve statistical significance. Sufficient numbers of bone marrow cells were obtained on the aspirates of one control and one drug treated mouse (numbers 191 and 195, respectively) to permit Southern analysis. Proviral signal was detectable only in the mouse that had received AP20187.

Effects of AP20187 on Hematopoietic Cells in the Spleen

After 40 days of drug administration, splenectomies were performed; spleens were weighed and spleen cells were tested in clonogenic assays to determine the frequency of genetically modified progenitor cells. Results are shown in Table 6.

TABLE 6

Effects of AP20187 on spleen size and G418 resistant colonies in the spleen

| | Spleen Weight (mg) | Mean (mg) | G418 Resistant (%) | Mean (%) |
|---|---|---|---|---|
| Control Group (%) | | | | |
| 188 | 120 | | 1.7% | |
| 190 | 90 | | 0.7% | |
| 191 | 101 | 112.2 (+/−16.3) | 3.7% | 2.4 (+/−1.7%) |
| 192 | 130 | | 4.7% | |
| 193 | 120 | | 1.1% | |
| AP20187 Treated Group | | | | |
| 194 | 200 | | 4.1% | |
| 195 | 190 | | 5.2% | |
| 196 | 279 | 208.9 (+/−43.5) | 6.4% | 9 (+/−8.7%) |
| 197 | 213 | | 24.5% | |
| 198 | 162 | | 4.8% | |

AP20187 administration was associated with an increased percentage of genetically modified progenitor cells in the spleen that did not achieve statistical significance. However, AP20187 administration was associated with a significant increase in spleen size. This finding suggests that AP20187 stimulates cell expansion in the spleen.

To characterize the types of cells expanding in response to AP20187, flow cytometry was performed using antibodies directed against myeloid (CD11b), erythroid (TER119), megakaryocytic (CD41), B-lymphoid (B-220) and T-lymphoid (CD3) cells. Results for each mouse are shown in TABLE 7, and mean values are provided in TABLE 8.

TABLE 7

Effects of AP20187 on hematopoietic cell subsets in the spleen of individual mice

| | TER119 | CD11b | CD41 | CD3 | B220 |
|---|---|---|---|---|---|
| Control Group | | | | | |
| 188 | 13.3 | 6.2 | 1.0 | 23.4 | 40.0 |
| 190 | 12.6 | 3.5 | 1.2 | 30.3 | 39.7 |
| 191 | 8.7 | 3.7 | 1.2 | 36.3 | 46.8 |
| 192 | 6.8 | 4.5 | 1.2 | 19.8 | 44.8 |
| 193 | 7.1 | 6.2 | 1.3 | 23.1 | 42.1 |
| AP20187 Treated Group | | | | | |
| 194 | 21.0 | 9.5 | 0.7 | 24.4 | 31.6 |
| 195 | 28.2 | 7.8 | 0.5 | 8.4 | 24.5 |
| 196 | 40.8 | 12.8 | 1.1 | 4.8 | 23.0 |
| 197 | 27.4 | 8.2 | 3.3 | 6.5 | 33.2 |
| 198 | 21.1 | 13.0 | 1.4 | 16.7 | 33.8 |

TABLE 8

Mean values and standard deviations (parentheses) for the data presented in TABLE 7

| | TER119 | CD11b | CD41 | CD3 | B220 |
|---|---|---|---|---|---|
| Control Group | 9.7 (3.1) | 4.8 (1.3) | 1.2 (0.1) | 24.7 (3.9) | 42.7 (3.1) |
| AP20187 Treated Group | 27.7 (8.1) | 10.2 (2.5) | 1.4 (1.1) | 12.2 (8.2) | 29.2 (5.1) |

Results indicate that AP20187 administration is associated with an increase in myeloid (CD11b-positive) and erythroid (TER119-positive) cells in the spleen.

Example 9

Isolation and Transduction of Human Progenitor and Stem Cells

Human hemopoietic cells are obtained either from the bone marrow or from the peripheral blood. Stem cells and progenitors can be harvested in low numbers from peripheral blood, however numbers of stem cells and progenitors in the peripheral blood can be dramatically increased by the administration of cytokines, most commonly granulocyte colony stimulating factor (GCSF), although other growth factors such as granulocyte macrophage colony stimulating factor (GMCSF), flt-3 ligand (FL) or stem cell factor (SCF) can also be used. This process, termed "stem cell mobilization," can also be induced by the administration of chemotherapy, or using non-growth factor molecules, for example antibodies to the cell adhesion molecule VLA-4. While stem cells and progenitors are among the cells collected, they comprise only a minority (usually <2%) of cells, and it is useful to enrich for stem cells and progenitors prior to transduction. A standard method of enriching for stem cells and progenitors is to select for cells bearing the membrane surface antigen, CD34, although other cell surface markers may also be used. Cells bearing CD34 may be enriched using a number of commercially available approaches, including the Ceprate LC system (CellPro, Bothell, Wash.) the Miltenyi system (Auburn, Calif.) the Baxter system or other commercially available systems, according to the manufacturer's instructions. These methods typically yield a population of CD34 cells that is 50% to >90% pure. These cells are then transduced by incubation in the presence of retrovirus-containing supernatant at 37 degrees for 24 hours, fresh retroviral supernatant is added and the incubation is continued for an additional 24 hours (total 48 hours). During the transduction cells are incubated in the presence of SCF, m3 and IL6.

Example 10

Figure 4:
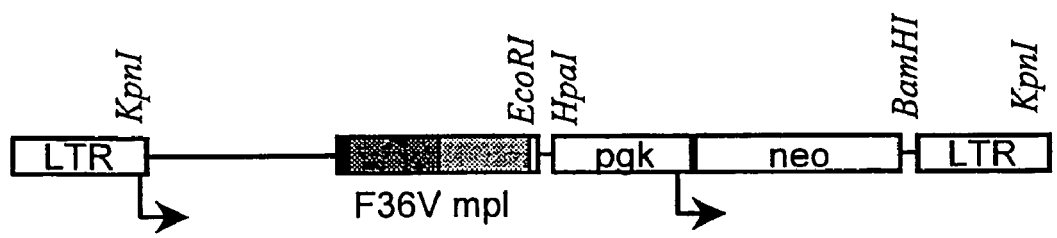
FIG. 4: MSCVneo-based retroviral vector encoding a fusion protein identical to F1mpl except for the presence of the F36V mutation. The MFM vector contains the F36Vmpl gene transcribed from the MSCV LTR (arrow) and the neo gene transcribed from the pgk promoter (arrow).

Amplification and Erythroid Differentiation of Human Cord Blood Cells by Activating C-MPL CD34+ cells were selected from human cord blood and transduced with a PG13-packaged, MSCV-based retrovirus vector encoding a dimerizer-responsive version of the c-mpl signaling domain (MFM, as described in Example 7, see FIG. 4). Activation of the c-mpl signaling domain through addition of AP1903 led to a 175-350-fold expansion in total cell numbers, in the absence of added cytokines. Cells emerging in response to the AP1903 were primarily erythroid, as evidenced by 90% of the cells expressing glycophorin by day 15 of culture. This finding was reproducible, occurring in each of four separate experiments.

These results indicate that dimerizing agents and constructs of the type described here can be used for the expansion of human hematopoietic cells.

Example 11

Stimulation of Cell Proliferation by Pharmacological Activation of gp130

Expression cassettes encoding fusion proteins containing the signaling domains of the gp130 fused to one, two or three copies of the FKBP12 domain were used to generate stably transfected Ba/F3 cell lines. The complexes that can be assembled in response to FK1012 differ for the various fusion proteins. In the presence of FK1012, fusion proteins containing a single FKBP domain are limited to simple dimerization, whereas proteins containing two or more FKBP domains can form both dimers and oligomers.

Dimerization of gp130-containing chimeric proteins containing a single FKBP12 domain resulted in minimal proliferative response to FK1012 or to the alternative synthetic dimerizer, AP1510. In contrast, cells expressing fusion proteins with two or three FKBP12 domains exhibited vigorous proliferative responses to AP1510, and lesser proliferative responses to FK1012. In one illustrative experiment, an MSCV-based expression vector was constructed that contained two FKBP12 domains. This MSCV construct employed a FKBP that had been modified to allow for binding to an alternative synthetic dimerizer, AP1903 (Clackson, et al., *PNAS* 95:10437, 1998). Expression of this construct in Ba/F3 cells allowed for a vigorous AP1903-dependent cell proliferation. These results suggest that gp130 generates a more potent proliferative stimulus in the context of an oligomeric complex than as a simple dimer.

Example 12

Use of Receptor Dimerization for Cardiac Repair

Myocardial infarctions heal by scar formation rather than muscle regeneration because surviving cardiocytes do not reenter the cell cycle after injury and because there are no muscle stem cells in heart (Quaini, et al. *Circ. Res.* 75:1050, 1994). Research has shown that skeletal and cardiac muscle cells can be grafted into injured hearts, where they form new muscle tissue in the injured region. Repair is always incomplete, however (Murry, et al. *J Clin Invest* 98:2512, 1996; Murry, et al. *Circulation* 92:1-12, 1995; Leor, et al. *Circulation* 94:11332, 1996; Scorcin, et al. *Circulation* 92(Suppl): 150, 1995). Skeletal myoblasts proliferate vigorously for a few days after transplantation but then permanently withdraw from the cell cycle and differentiate as local growth factors are depleted. Cardiac muscle cells from fetal or neonatal donors proliferate weakly after grafting for ~1 week and then also withdraw from the cell cycle. Furthermore, most of the cardiocytes undergo apoptosis after grafting, precluding formation of new myocardium.

Forced dimerization of appropriate receptors should have two salutary effects on forming new contractile tissue in the injured heart. First, controlled activation of mitogenic receptors (e.g. the FGF or IGF-1 receptors) should increase proliferation of cells after grafting. Second, activation of survival receptors (e.g. the gp130 receptor) should diminish apoptosis after grafting. Detailed methods to accomplish muscle repair through the use of the inventive compositions and methods for drug induced dimerization are provided for skeletal muscle cells and cardiac muscle cells.

Skeletal Muscle.

Skeletal muscle stem cells (satellite cells) are obtained from the limbs of mice or rats by standard enzymatic digestion followed by purification over a Percoll gradient. Satellite cells are grown in Ham's F10 containing 15% horse serum, with 6 ng/ml basic FGF added twice daily. Satellite cells are transfected with a replication-deficient retrovirus encoding the receptor of interest, using the technique of Springer and Blau (*Somat. Cell Mol. Genet.* 23:203, 1997). In brig this approach uses serial centrifugation to increase collisions between retroviral particles and cell receptors, resulting in >90% transfection efficiency. After centrifugation, the retrovirally transfected cells are selected either by antibiotic resistance or by expression of an indicator such as GFP.

Cells are grafted into myocardial injuries as described by Murry, et al. (*J. Clin. Invest.* 98:2512, 1996). Briefly, the procedure involves creating cardiac injury through coronary ligation or myocardial freezing in open-chest, anesthetized animals. At the desired time after the injury, a suspension of transfected, syngeneic muscle cells is injected directly into the lesion using a syringe and needle. The dimerization drug is then administered to the animal to activate either cell proliferation or survival.

The effect of receptor dimerization is monitored histologically by determining graft size, graft cell proliferation kinetics, and determining whether the grafts restore contractile function to the injured heart.

A comparable protocol can be used in humans as well. In this case autologous human satellite cells are obtained from muscle biopsies, transfected, and reimplanted into the heart by intracoronary infusion or intramyocardial injection.

Cardiac Muscle

Two approaches are used with cardiac myocytes. The first follows a protocol similar to that proposed for satellite cells. Cardiac myocytes are isolated from fetal mice or rats by enzymatic digestion and maintained in M199/DMEM with 15% FBS. Cardiomyocytes are retrovirally transfected using a centrifugation protocol similar to that described for satellite cells. Alternatively, cardiomyocytes can be transfected by exposure to high titer retrovirus in a Transwell coculture system. Transfected cells are selected by antibiotic resistance or expression of GFP; expansion of transfected cells may be facilitated in vitro by addition of the dimerization agent.

The second approach takes advantage of the recent discovery of human embryonic stem (ES) cells. Undifferentiated stem cells are stably transfected with a retrovirus encoding the receptor of interest. In addition, however, a second gene is inserted which permitted selection of cells which have undergone cardiac differentiation, e.g. the use of a cardiac promoter driving a selectable marker (see for example, Klug, et al. *J. Clin. Invest.* 98:216, 1996)). After selecting for cells transfected with the receptor gene, the ES cells are allowed to differentiate, and subsequently those that undergo cardiac differentiation are selected. Growth of these cells also may be facilitated in vitro by addition of the dimerization agent.

After selection, the transfected cardiomyocytes are engrafted into injured hearts as described for the skeletal myoblasts. The effects of the dimerization system are determined by measuring graft cell survival, proliferation, final graft size, and effect on contractile function.

Example 13

Dimerizer-Mediated Induction of Hepatocyte Proliferation

Under physiological conditions the liver is a quiescent organ with only 1 out of 20,000 hepatocytes dividing at any given time point. Primary hepatocytes isolated from livers by collagenase perfusion usually do not proliferate in culture. However, one or two rounds of hepatocyte division in vitro can be induced by growth factors such as HGF or EGF. Non-physiological high concentrations of HGF can also induce hepatocellular replication in vivo during the time of intravenous HGF infusion. This indicates that stimulation of only one signaling pathway (via the HGF receptor c-met) may be sufficient for hepatocytes to exit the G0 phase and enter the cell cycle.

FKBP ligand homodimers (AP1903 or AP20187) can be used to activate cellular signaling pathways in hepatocytes that express gene fusions between appropriate signaling domains and a mutated form of FKBP (F36V-TABLE 1). The ability to induce proliferation of primary human hepatocytes in vitro and in vivo has at least two lines of potential applications.

First, expansion of primary human hepatocytes may provide an alternative or adjunct to traditional liver transplantation procedures. Liver transplantation is a routine technique to treat a number of fatal liver diseases including hepatic tumors, HCV-associated liver cirrhosis, and genetic diseases. Due to the shortage of donor livers, hepatocyte transplantation into patients may be an alternative to cover the period until a HLA-compatible liver is available for transplantation. In this context, expansion of primary human hepatocytes in culture without significant dedifferentiation in order to obtain a sufficient cell number as source for transplantation and the establishment of a representative selection of cryo-conserves with different HLA-phenotypes would be beneficial. As a more elegant alternative, in vivo expansion of transplanted hepatocytes depending on a synthetic drug would be even more desired and may replace liver transplantation.

Second, controlled expansion of liver cells in vivo and in vitro may assist in the development of small transgenic animals that have "humanized" livers that can be used to investigate human liver infectious agents. The infectious agents causing a number of diseases in human including malaria and viral hepatitis (HCV, HBV) demonstrate a restricted tropism to human hepatocytes. As a model for studying therapeutic approaches often only chimpanzees are available. The creation of a small animal with a "humanized" liver by in vivo expansion of transplanted human hepatocytes in immunodeficient mice would be crucial for testing of anti HCV ribozyme-based or HCV protease mediated approaches for treatment of HCV infection.

Tissue culture model: The isolation of primary human hepatocytes by collagenase perfusion is labor intensive, besides human donor livers are difficult to obtain. Moreover, hepatocytes isolated from different donor livers may differ in their response to proliferation stimuli. As a more standardized system, a non-transformed cell line derived from primary monkey (*Maccaca fasciculata*) hepatocytes (MIT) by culturing under unique conditions was used to investigate dimerizer-mediated induction of hepatocyte proliferation. This cell line was developed by Irina Kirillova and Nelson Fausto (Department of Pathology, University of Washington). MH cells express all markers for differentiated hepatocytes including albumin, α1-antitrypsin, and cytokeratin 18.

To test the proliferation properties of MH cells, cellular DNA replication based on incorporation of BrdU was analyzed. $5 \times 10^4$ MH cells were plated per well (24 well plate). 16 hours later cells were washed with PBS and incubated under different conditions: −FCS=serum-free, +FCS=medium was supplemented with 10% FCS, or +HGF=medium was supplemented with 300 ng/ml recombinant HGF. The corresponding medium was changed daily. At different time point BrdU was added for 4 hours to one set of cells. After this, BrdU labeled DNA was detected in cell nuclei by immuno-histochemistry with BrdU-specific antibodies.

Generally, most cell types that passed the G1 checkpoint and entered the S-phase are committed to complete the cell cycle with cell division. However, under specific conditions, cells (including hepatocytes) that had passed the S-phase can exit the cell cycle at the G2 check-point without mitosis. Therefore, DNA replication in MH cells as a more direct way to study signaling pathways was analyzed. Cellular DNA synthesis in MH cells was found to depend upon the presence of HGF or FCS. The percentage of BrdU labeled cells dropped from ~50 to 5% if cells were deprived of serum and HGF for 6 days. Incubation with FCS and HGF had an additive effect on stimulation of DNA replication.

Gene transfer into MH cells: The fusion proteins between a mutated form of FKBP and the signaling domain of cellular receptors derived from the receptors shown in TABLE 9.

TABLE 9

Chimeric receptors used in hepatocyte experiments

| Receptor | Natural Ligand | Species | Retrovirus |
|---|---|---|---|
| c-met | Hepatocyte growth factor (HGF) | Human | MSCVF36V-cmet |
| Epo-R | Erythropoietin | Murine | MSCVF2'-epoR |
| Mpl | Thrombopoietin (Tpo) | Human | MSCVF2'-hmpl |
| Mpl | Thrombopoietin (Tpo) | Murine | MSCVF2'-mpl |
| EGF-R | Epithelial growth factor (EGF) | Murine | MSCVF36V-egfR |
| gp130 | Interleukine 6 (IL-6) | Human | MSCVF2'-gp130 |
| G-CSF-R | Granulocyte stimulating factor (GCSF) | Murine | MSCVF2'-gcsfk |
| G-CSF-R | Granulocyte stimulating factor (GCSF) | Human | MSCVF36V-hgcsfR |

The receptors c-met, EGF, gp130, and mpl are normally expressed in hepatocytes. The presence of the other receptors on hepatocyte cell surfaces has yet to be clarified. F36V is a single copy variant of FKBP with a Ser to Val substitution at position 36, that can bind a synthetic dimerizer drug (AP1903, AP10189) with nanomolar affinity and 1,000 fold higher selectivity compared to the endogenous FKBP. F2' encodes a fusion protein containing two identical copies of the F36V modified drug binding domain that are encoded by nonidentical DNA sequences in order to reduce recombination in retroviruses. Several of the chimeric receptors noted in TABLE 9 contain a myristoylation domain targeting the protein for membrane anchoring and a HA.11 epitope.

Retroviruse vectors expressing the chimeric receptors provided in TABLE 9 were prepared as a means for gene transfer into hepatocytes. The retroviruse vectors were derived from MSCVneo, with the gene for the chimeric receptor under transcription control of the retroviral LTR and the neo gene transcribed from the PGK promoter. All variants were produced in ecotropic and in amphotropic packaging cell lines with titers ranging from $1 \times 10^3$ to $1 \times 10^4$ cfu/ml. The viruses were titered on 208f rat fibroblasts based on the number of G418 resistant colonies. Next, the percentage of MH cells grown in the presence of FCS and HGF that can be transduced by an amphotropic β-Gal virus after an incubation of 5 hours at an MOI of 1 cfu per cell was determined. Under these infection conditions 40% of MH cells expressed the reporter gene β-galactosidase. Exactly the same conditions were used for infection with amphotropic viruses expressing chimeric receptors. FCS and HGF starvation of MH cells was started 24 hours after infection. $5 \times 10^4$ MH cells were plated per well (24 well plate) in the presence of FCS. 24 hours after retrovirus infection, culture medium was replaced by serum-free medium and cells were starved for 6 days. At this time point AP20187 was added to one set of cells and BrdU incorporation was measured three days after induction. BrdU labeled cells were counted in four independent areas for each sample (N=3) and expressed as the percentage of BrdU (+) cells. BrdU incorporation was analyzed 3 days after AP20187 stimulation. Two other groups of samples were analyzed for BrdU incorporation after 6 days or 9 days of AP20187 stimulation (AP20187 in the culture medium was renewed every 3 days). The results obtained at different time points after addition of AP20187 did not differ significantly.

Figure 5:
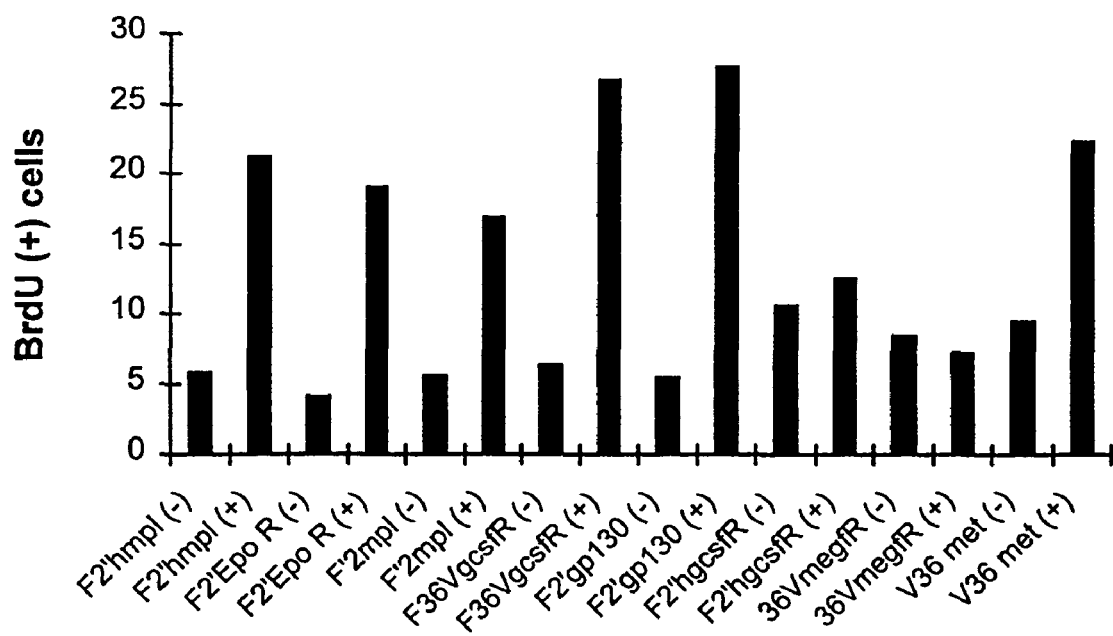
FIG. 5. DNA synthesis in MH cells expressing FKBP chimeric receptors after stimulation with AP20187. $5 \times 10^4$ MH cells were plated per well (24 well plate) in the presence of FCS. 24 hours after retrovirus infection, culture medium was replaced by serum-free medium and cells were starved for 6 days. At this time point AP20187 was added to one set of cells and BrdU incorporation was measured three days after induction. BrdU labeled cells were counted in four independent areas for each sample (N=3) and expressed as the percentage of BrdU (+) cells. The (+) and (−) symbols after the chimeric gene designations indicates the presence and absence of AP20187, respectively. The amount of BrdU incorporation has been corrected to account for the amount of BrdU incorporation measure in control cells both in the presence and absence of AP20187.

The results of these experiments are set forth in FIG. 5. As shown in FIG. 5, the (+) and (−) symbols after the chimeric gene designations indicates the presence and absence of AP20187, respectively. The expression of chimeric receptors in arrested MH cells results in a ~two-fold stimulation of replication in the absence of AP20187. This is particularly the case for cells infected with retroviral vectors containing F2'-hgcsfR, F36V-cmet, and F36VmegfR. The addition of the dimerizer, AP20187, has a clear effect on DNA proliferation in MH expressing chimeric receptors, which is greater than the nonspecific induction by AP20187 alone. The highest DNA synthesis induction rates were observed for F2' hmpl, F2'EpoR, F2'mpl, F36VgcsfR, and F2gp130.

Each of the patent documents and scientific papers identified herein is hereby incorporated by reference. Those documents serve to illustrate the state of the art in various aspects of this invention. While the preferred embodiment of the invention has been illustrated and described, it will be appreciated that various changes can be made therein without departing from the spirit and scope of the invention.

Numerous modifications and variations of the present invention should be apparent to one of skill in the art. Such modifications and variations, including design choices in selecting a signaling domain, ligand-binding domain, ligand, fusion protein design, DNA formulation, viral vector or other DNA delivery means, manner and route of transgene administration, etc., are intended to be encompassed by the scope of the invention and of the appended claims.

The invention claimed is:

1. A method for rendering a subpopulation of mammalian hematopoietic stem cells susceptible to divalent ligand-induced growth, proliferation or differentiation, which method comprises
    transducing one or more cells of a population of mammalian primary hematopoietic stem cells with at least one retroviral vector comprising at least one recombinant DNA construct encoding a fusion protein which comprises at least one signaling domain derived from an intracellular portion of a thrombopoietin receptor and at least one ligand-binding domain derived from F36V which is heterologous with respect to the signaling domain and binds to a selected divalent ligand capable of inducing association of two or more molecules of F36V such that upon exposure of the transduced cells to a concentration of the divalent ligand having the formula:

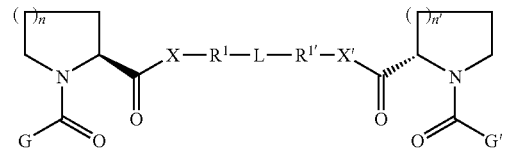

effective to induce association of two or more of the encoded fusion proteins, growth, proliferation or differentiation of said cells is induced;
    wherein X and X' can be O, NH, or $CH_2$;
    L is a covalently linker moiety;
    wherein G and G' are independently selected from the group comprised of

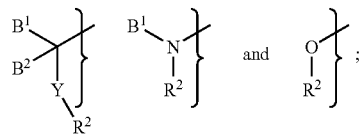

$B^1$ and $B^2$ are each independently hydrogen, alkyl, alkenyl, alkynyl, cycloalkyl, cycloalkenyl, cycloalkynl, heteroalkyl, heteroalkenyl, heteroalkynyl, heterocycloalkyl, heterocycloalkenyl, heterocycloalkynyl, substituted aryl, aryl, or heteroaryl moieties;
    Y is O, S, NH, —NH(C=O)—, NH(C=O)—O—, NH(SO_2)—, $NR_3$, or a covalent bond;
    $R^1$, $R^{1'}$, and $R^2$ are the same or different and are each independently hydrogen, alkyl, alkenyl, alkynyl, cycloalkyl, cycloalkenyl, cycloalkynyl, hetero alkyl, heteroalkenyl, heteroalkynyl, heterocycloalkyl, heterocycloalkenyl, heterocycloalkayl, substituted aryl, aryl, or heteroaryl moieties;
    n and n' are each independently 1 or 2;
    wherein at least one of X—$R^1$ and X'—$R^{1'}$ is independently a moiety:

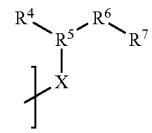

wherein $R^4$ is hydrogen; branched, unbranched, cyclic, saturated or unsaturated, substituted or unsubstituted aliphatic; branched, unbranched or cyclic heteroaliphatic; aryl or heteroaryl;
    $R^5$ is a branched, unbranched or cyclic, aliphatic moiety of 1 to 8 carbon atoms;
    $R^6$ is a substituted or unsubstituted aliphatic, heteroaliphatic, heterocyclic, aryl or heteroaryl moiety;
    $R^7$ is hydrogen or a reactive functional group permitting covalent attachment to a linker moiety; and
    wherein the transduction is carried out in vivo or ex vivo and wherein said transduced cells are suitable for introduction into a mammal.

2. The method of claim 1, wherein the subpopulation of mammalian primary hematopoietic stem cells comprises at least one of bone marrow cells, cord blood cells, and peripheral blood cell.

3. The method of claim 1, wherein the mammalian primary hematopoietic stem cells are human cells.

4. The method of claim 1 wherein the cells are removed from the mammal prior to being transduced with the retroviral vector comprising at least one recombinant DNA construct.

5. The method of claim 4 which further comprises introducing the transduced cells so obtained into a mammal.

6. The method of claim 5 wherein the transduced cells are treated with divalent ligand prior to their introduction into the mammal.

7. The method of claim 5 wherein the cells are allogeneic with respect to the mammal.

8. The method of claim 5 wherein the cells are syngeneic with respect to the mammal.

9. The method of claim 5 wherein the cells are autologous with respect to the mammal.

10. The method of claim 5 wherein the mammal is a human.

11. The method of claim 1 wherein the cells are transduced within the mammal.

12. A method for expanding a subpopulation of mammalian hematopoietic stem cells comprising:
(a) providing a subpopulation of mammalian primary hematopoietic stem cells which has been transduced with at least one retroviral vector comprising at least one recombinant DNA construct encoding a fusion protein which (i) comprises at least one signaling domain derived from a thrombopoietin receptor and at least one divalent ligand-binding domain derived from F36V, and (ii) induces growth, proliferation or differentiation upon multimerization with one or more other fusion proteins containing at least one signaling domain; and
(b) treating the subpopulation of cells with a concentration of a divalent ligand capable of inducing association of two or more molecules of F36V having the formula:

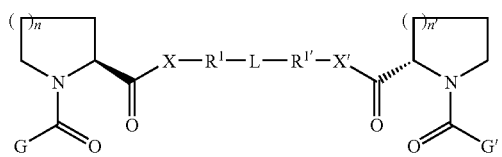

effective to induce association of two or more of the encoded fusion proteins, growth, proliferation or differentiation of said cells is induced;
wherein X and X' can be O, NH, or CH$_2$;
L is a covalently linker moiety;
wherein G and G' are independently selected from the group comprised of

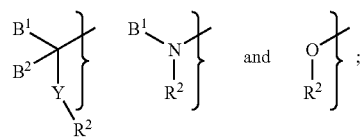

B$^1$ and B$^2$ are each independently hydrogen, alkyl, alkenyl, alkynyl, cycloalkyl, cycloalkenyl, cycloalkynl, heteroalkyl, heteroalkenyl, heteroalkynyl, heterocycloalkyl, heterocycloalkenyl, heterocycloalkynyl, substituted aryl, aryl, or heteroaryl moieties;
Y is O, S, NH, —NH(C═O)—, NH(C═O)—O—, NH(SO$_2$)—, NR$_3$, or a covalent bond;

R$^1$, R$^{1'}$, and R$^2$ are the same or different and are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkayl, substituted aryl, aryl, or heteroaryl moieties;
n and n' are each independently 1 or 2;
wherein at least one of X—R$^1$ and X'—R$^{1'}$ is independently a moiety:

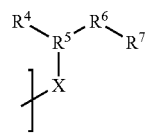

wherein R$^4$ is hydrogen; branched, unbranched, cyclic, saturated or unsaturated, substituted or unsubstituted aliphatic; branched, unbranched or cyclic heteroaliphatic; aryl or heteroaryl;
R$^5$ is a branched, unbranched or cyclic, aliphatic moiety of 1 to 8 carbon atoms;
R$^6$ is a substituted or unsubstituted aliphatic, heteroaliphatic, heterocyclic, aryl or heteroaryl moiety;
R$^7$ is hydrogen or a reactive functional group permitting covalent attachment to a linker moiety; and
wherein said treatment with said divalent ligand is carried out in vivo or ex vivo, and wherein said transduced cells are suitable for introduction into a mammal.

13. The method of claim 12, wherein the subpopulation of mammalian primary hematopoietic stem cells comprises at least one of bone marrow cells, cord blood cells, and peripheral blood cells.

14. The method of claim 12, wherein the mammalian primary hematopoietic stem cells are human cells.

15. The method of claim 12 wherein the subpopulation of mammalian primary hematopoietic stem cells which has been transduced with the at least one retroviral vector was transduced ex vivo.

16. The method of claim 15 which further comprises introducing the transduced cells so obtained into a recipient mammal.

17. The method of claim 16 wherein the transduced cells are treated with the divalent ligand prior to their introduction into the recipient mammal.

18. The method of claim 16 wherein the cells are allogeneic with respect to the mammal.

19. The method of claim 16 wherein the cells are syngeneic with respect to the mammal.

20. The method of claim 16 wherein the cells are autologous with respect to the mammal.

21. The method of claim 16 wherein the mammal is a human.

22. The method of claim 12 wherein the subpopulation of mammalian primary hematopoietic stem cells which has been transduced with the at least one retroviral vector was transduced within the mammal.

23. The method of claim 12, wherein the cells are treated with the divalent ligand ex vivo.

24. The method of claim 12, wherein the cells are treated with the divalent ligand in vivo.

25. A method for treating or preventing a hemopoietic disease or pathological condition in a mammal, comprising introducing into the mammal a subpopulation of cells produced by the method of either claim 2 or claim 13.

26. The method of claim 25 which further comprises administering to the mammal a divalent ligand having the formula:

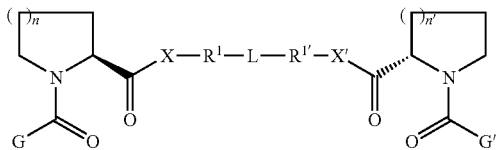

wherein X and X' can be O, NH, or $CH_2$;
L is a covalently linker moiety;
wherein G and G' are independently selected from the group comprised of

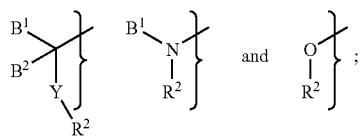

$B^1$ and $B^2$ are each independently hydrogen, alkyl, alkenyl, alkynyl, cycloalkyl, cycloalkenyl, cycloalkynl, heteroalkyl, heteroalkenyl, heteroalkynyl, heterocycloalkyl, heterocycloalkenyl, heterocycloalkynyl, substituted aryl, aryl, or heteroaryl moieties;
Y is O, S, NH, —NH(C=O)—, NH(C=O)—O—, $NH(SO_2)$—, $NR_3$, or a covalent bond;
$R^1$, $R^{1'}$, and $R^2$ are the same or different and are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkayl, substituted aryl, aryl, or heteroaryl moieties;
n and n' are each independently 1 or 2;
wherein at least one of X—$R^1$ and X'—$R^1$ is independently a moiety:

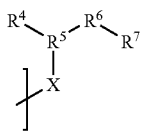

wherein $R^4$ is hydrogen; branched, unbranched, cyclic, saturated or unsaturated, substituted or unsubstituted aliphatic; branched, unbranched or cyclic heteroaliphatic; aryl or heteroaryl;
$R^5$ is a branched, unbranched or cyclic, aliphatic moiety of 1 to 8 carbon atoms;
$R^6$ is a substituted or unsubstituted aliphatic, heteroaliphatic, heterocyclic, aryl or heteroaryl moiety; and
$R^7$ is hydrogen or a reactive functional group permitting covalent attachment to a linker moiety.

27. A method for treating or preventing a hemopoietic disease or pathological condition in a mammal, comprising expanding a subpopulation of hemopoietic cells by the method of claim 13 and introducing the resultant cells to the mammal.

28. The method according to claim 1, wherein said divalent ligand is selected from the group consisting of AP1903, AP20187, and AP1510.

29. The method of claim 12, wherein said divalent ligand is selected from the group consisting of AP1903, AP20187, and AP1510.

30. The method of claim 26, wherein said divalent ligand is selected from the group consisting of AP1903, AP20187, and AP1510.

31. A method for expanding an erythroid cell population comprising:
(a) providing CD34+ primary hematopoietic stem cells transduced with a retroviral vector comprising at least one recombinant DNA construct that encodes a fusion protein that (i) comprises at least one signaling domain derived from a thrombopoietin receptor and at least one divalent ligand-binding domain derived from F36V, and (ii) induces growth, proliferation or differentiation upon multimerization with one or more other fusion proteins containing at least one signaling domain; and
(b) treating the transduced cells with a concentration of a divalent ligand capable of inducing association of two or more molecules of F36V having the formula:

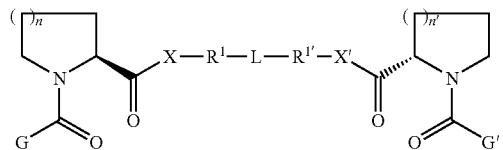

wherein X and X' can be O, NH, or $CH_2$;
L is a covalently linker moiety;
wherein G and G' are independently selected from the group comprised of

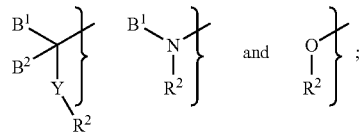

$B^1$ and $B^2$ are each independently hydrogen, alkyl, alkenyl, alkynyl, cycloalkyl, cycloalkenyl, cycloalkynl, heteroalkyl, heteroalkenyl, heteroalkynyl, heterocycloalkyl, heterocycloalkenyl, heterocycloalkynyl, substituted aryl, aryl, or heteroaryl moieties;
Y is O, S, NH, —NH(C=O)—, NH(C=O)—O—, $NH(SO_2)$—, $NR_3$, or a covalent bond;
$R^1$, $R^{1'}$, and $R^2$ are the same or different and are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkayl, substituted aryl, aryl, or heteroaryl moieties;
n and n' are each independently 1 or 2;
wherein at least one of X—$R^1$ and X'—$R^{1'}$ is independently a moiety:

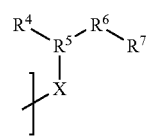

wherein $R^4$ is hydrogen; branched, unbranched, cyclic, saturated or unsaturated, substituted or unsubstituted aliphatic; branched, unbranched or cyclic heteroaliphatic; aryl or heteroaryl;

$R^5$ is a branched, unbranched or cyclic, aliphatic moiety of 1 to 8 carbon atoms;

$R^6$ is a substituted or unsubstituted aliphatic, heteroaliphatic, heterocyclic, aryl or heteroaryl moiety; and $R^7$ is hydrogen or a reactive functional group permitting covalent attachment to a linker moiety;

wherein said treatment with said divalent ligand is carried out in vivo or ex vivo;

wherein said treatment results in expansion of erythroid cells from the transduced cells; and wherein said transduced cells are suitable for introduction into a mammal.

32. The method of claim 31, wherein said divalent ligand is selected from the group consisting of AP1903, AP20187, and AP1510.

* * * * *

UNITED STATES PATENT AND TRADEMARK OFFICE
CERTIFICATE OF CORRECTION

PATENT NO. : 7,754,202 B1  Page 1 of 1
APPLICATION NO. : 09/582916
DATED : July 13, 2010
INVENTOR(S) : Carl Anthony Blau and David M. Spencer It is certified that error appears in the above-identified patent and that said Letters Patent is hereby corrected as shown below:

In the Specification
Please insert after the Title, col. 1, line 4:

--This invention was made with government support under grant numbers 1 RO1 DK52997-01 and DK47754 awarded by National Institutes of Health. The government has certain rights in the invention.--

Signed and Sealed this
Twenty-first Day of June, 2011

David J. Kappos
*Director of the United States Patent and Trademark Office*